United States Patent
Jones et al.

(10) Patent No.: US 11,351,055 B2
(45) Date of Patent: Jun. 7, 2022

(54) PERFORATED OSTOMY BARRIER EXTENDER

(71) Applicant: Hollister Incorporated, Libertyville, IL (US)

(72) Inventors: Susan R. Jones, Grayslake, IL (US); Jennifer A. Capaul, Vernon Hills, IL (US); Christina Augustyn, Chicago, IL (US)

(73) Assignee: Hollister Incorporated, Libertyville, IL (US)

( * ) Notice: Subject to any disclaimer, the term of this patent is extended or adjusted under 35 U.S.C. 154(b) by 303 days.

(21) Appl. No.: 16/094,132

(22) PCT Filed: May 3, 2017

(86) PCT No.: PCT/US2017/030761
§ 371 (c)(1),
(2) Date: Oct. 16, 2018

(87) PCT Pub. No.: WO2017/192669
PCT Pub. Date: Nov. 9, 2017

(65) Prior Publication Data
US 2019/0125570 A1 May 2, 2019

Related U.S. Application Data

(60) Provisional application No. 62/331,119, filed on May 3, 2016.

(51) Int. Cl.
*A61F 5/448* (2006.01)
*A61F 5/445* (2006.01)
(Continued)

(52) U.S. Cl.
CPC .............. *A61F 5/448* (2013.01); *A61F 5/443* (2013.01); *A61F 5/4404* (2013.01); *A61F 5/445* (2013.01)

(58) Field of Classification Search
CPC .......... A61F 5/445; A61F 5/448; A61F 13/00; B65D 2203/00; G09F 2003/0269; B31D 1/026
See application file for complete search history.

(56) References Cited

U.S. PATENT DOCUMENTS 5,203,806 A * 4/1993 Broida ................ A61F 5/445
604/332
6,875,200 B1 4/2005 Ajagbe
(Continued)

FOREIGN PATENT DOCUMENTS

EP 2904996 A1 8/2015
WO 0154632 A1 8/2001
(Continued)

OTHER PUBLICATIONS

International Preliminary Report on Patentability issued by International Bureau in connection with PCT/US2017/030761 dated Nov. 15, 2018.

*Primary Examiner* — Tatyana Zalukaeva
*Assistant Examiner* — Meagan Ngo
(74) *Attorney, Agent, or Firm* — Levenfeld Pearlstein, LLC

(57) ABSTRACT

An ostomy barrier extender includes a skin friendly adhesive layer, a backing layer laminated on a surface of the skin friendly adhesive layer, a release liner laminated on an opposite surface of the skin friendly adhesive layer, at least one perforated feature, an outer periphery, an inner periphery, and a ring shaped body defined between the outer periphery and the inner periphery. The ostomy barrier extender is configured to separate along at least one perforated feature.

14 Claims, 18 Drawing Sheets

(51) Int. Cl.
*A61F 5/44* (2006.01)
*A61F 5/443* (2006.01)

(56) References Cited

U.S. PATENT DOCUMENTS

| | | | |
|---|---|---|---|
| 2003/0060786 A1* | 3/2003 | Olsen | A61F 5/448 604/342 |
| 2007/0078418 A1* | 4/2007 | May | A61F 5/443 604/336 |
| 2009/0182293 A1* | 7/2009 | Redlich | A61F 5/445 604/342 |
| 2010/0217215 A1* | 8/2010 | Lykke | A61L 15/26 604/344 |
| 2016/0235582 A1* | 8/2016 | Moavenian | A61F 5/443 |
| 2017/0007440 A1* | 1/2017 | Moavenian | A61F 5/445 |

FOREIGN PATENT DOCUMENTS

| | | | |
|---|---|---|---|
| WO | 2011015201 A1 | 2/2011 | |
| WO | WO-2015052092 A1 * | 4/2015 | A61F 5/448 |

* cited by examiner

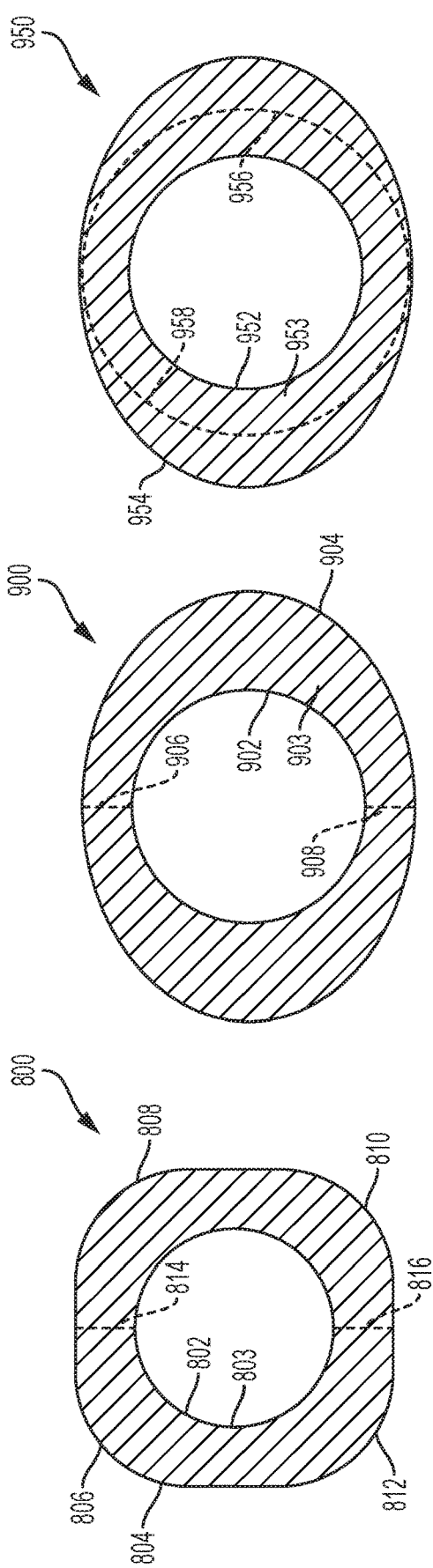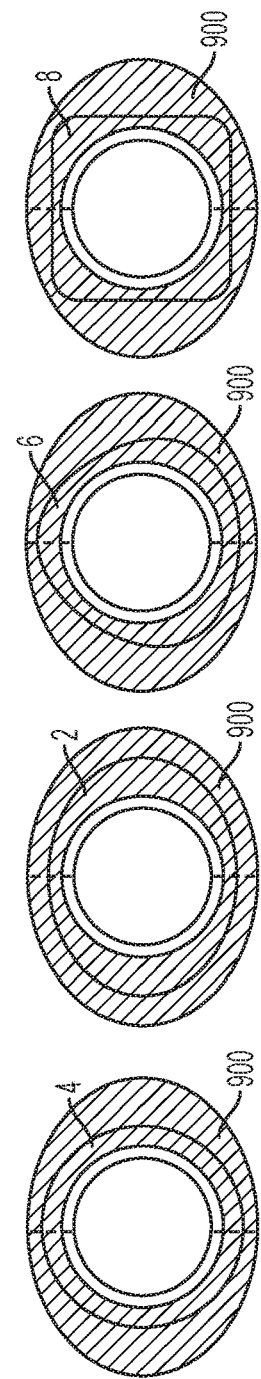

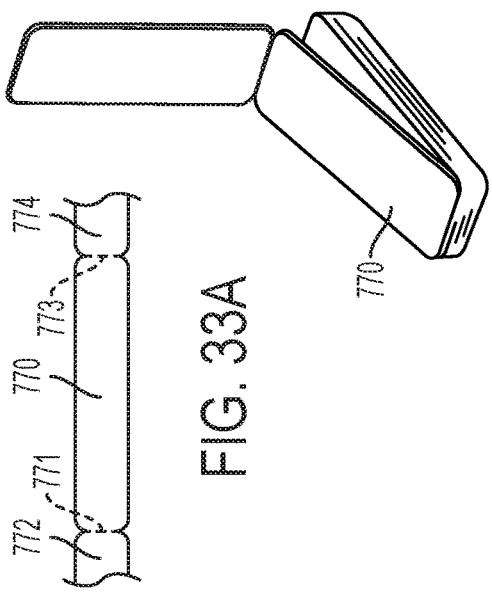
FIG. 33A
FIG. 33B
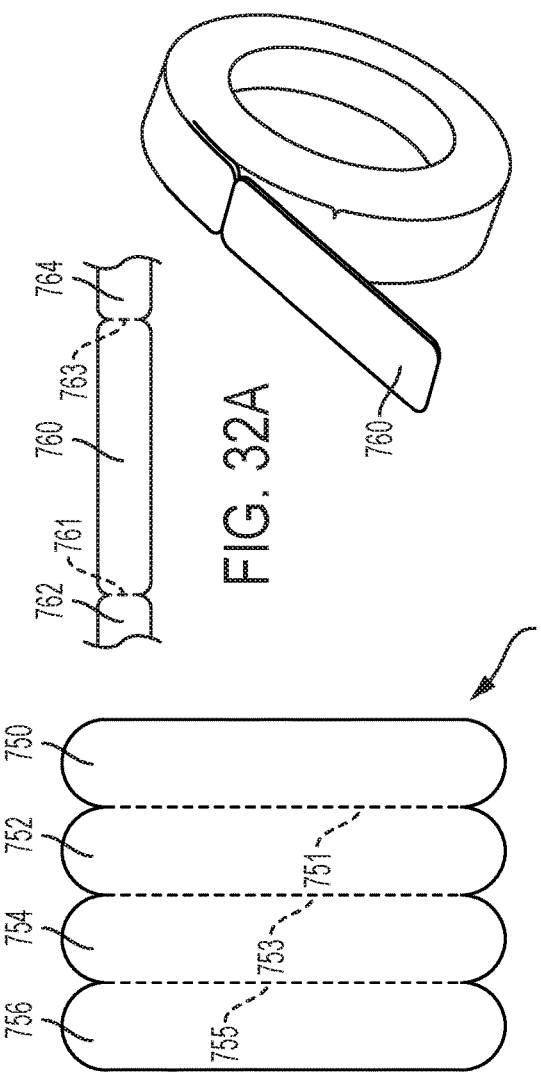
FIG. 32A
FIG. 32B
FIG. 31
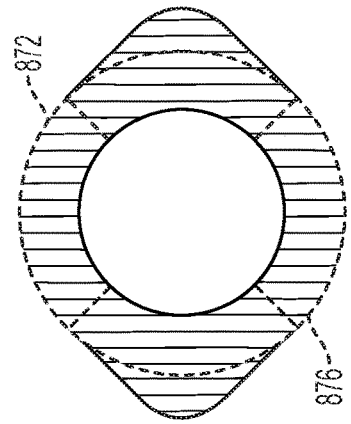
FIG. 34C
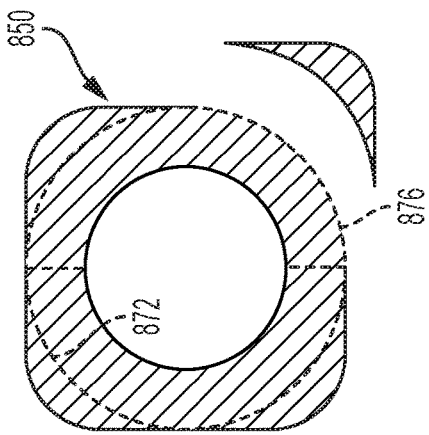
FIG. 34B
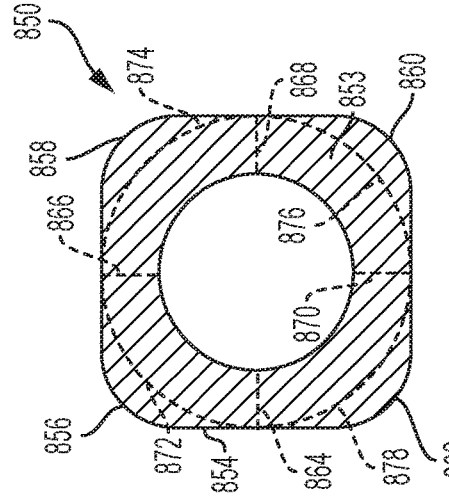
FIG. 34A

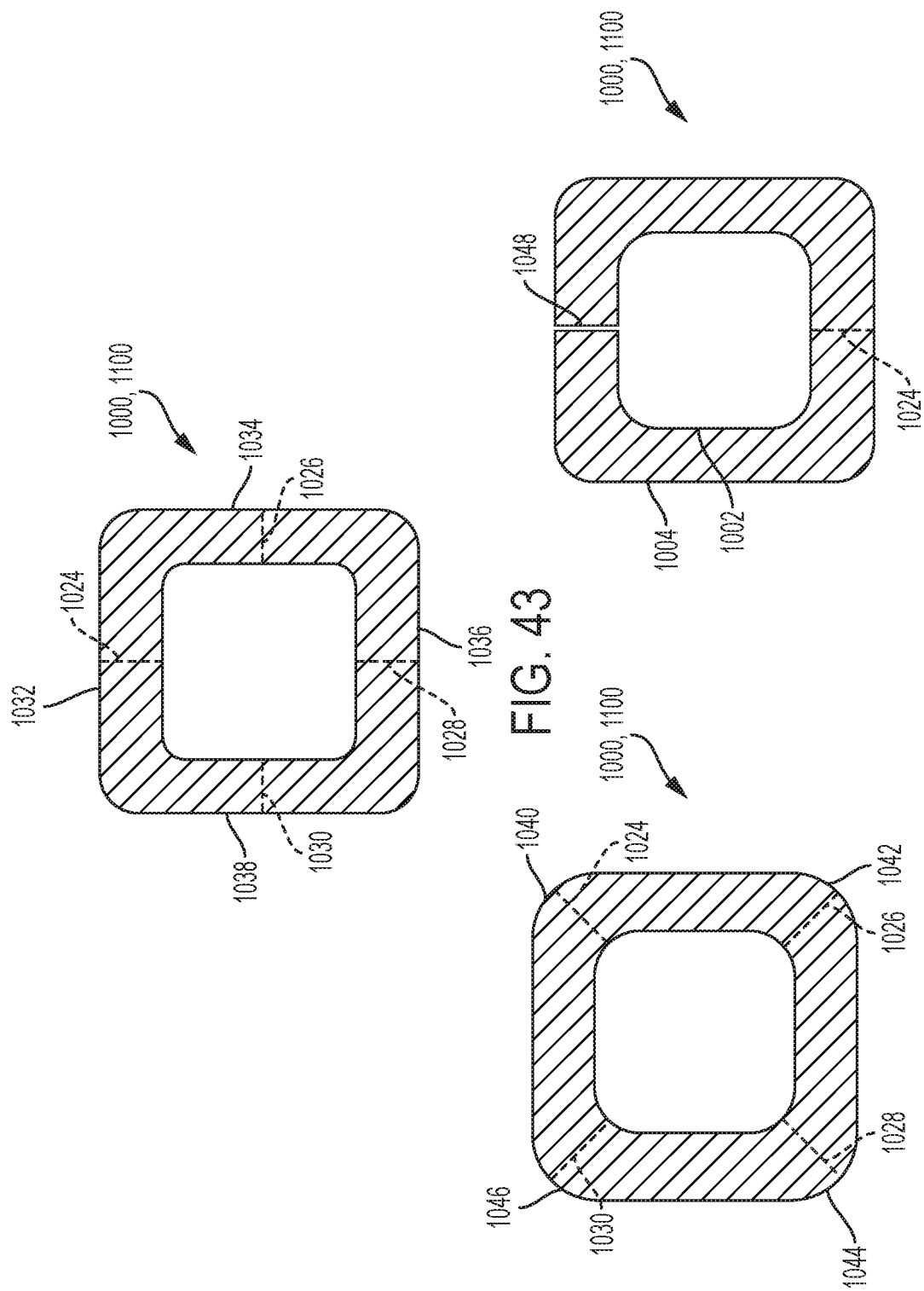

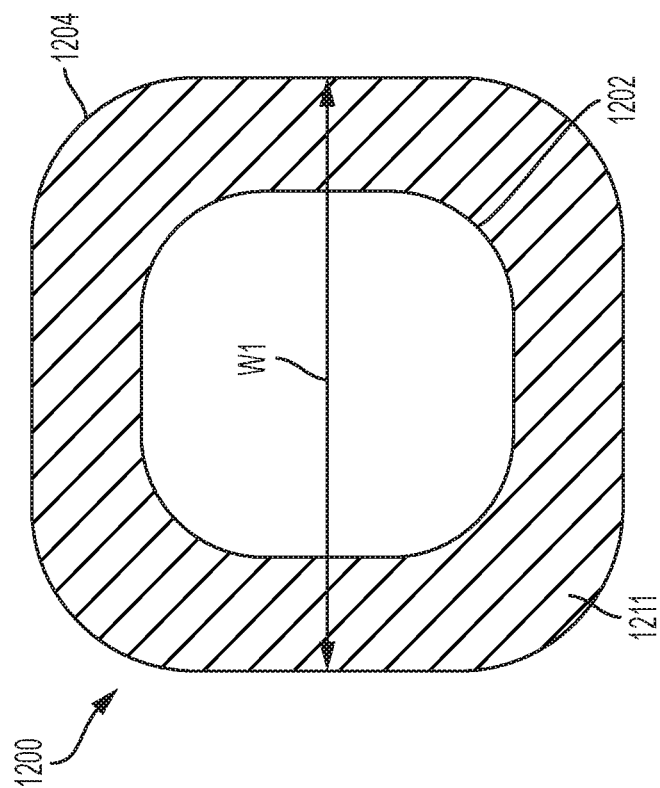
FIG. 46
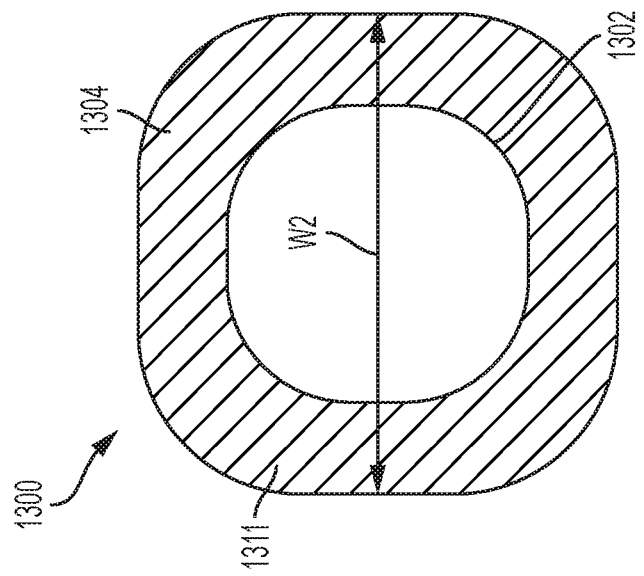
FIG. 47
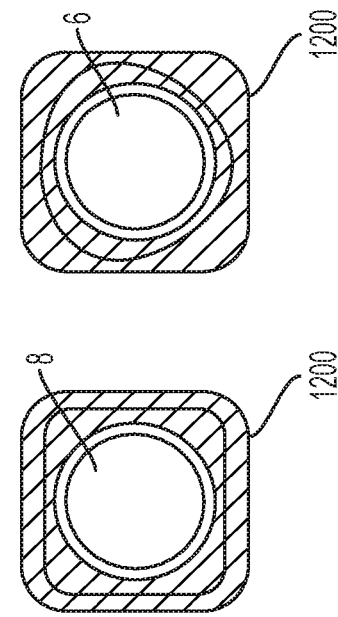
FIG. 48
FIG. 49
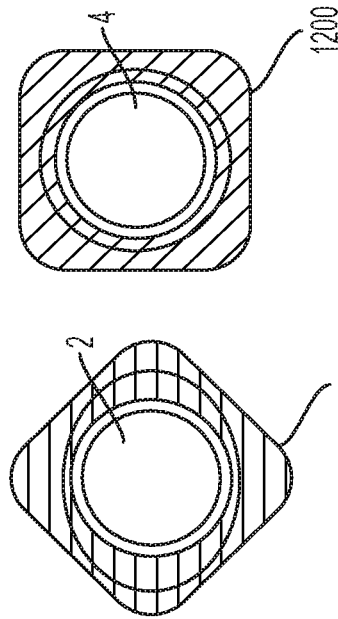
FIG. 50
FIG. 51

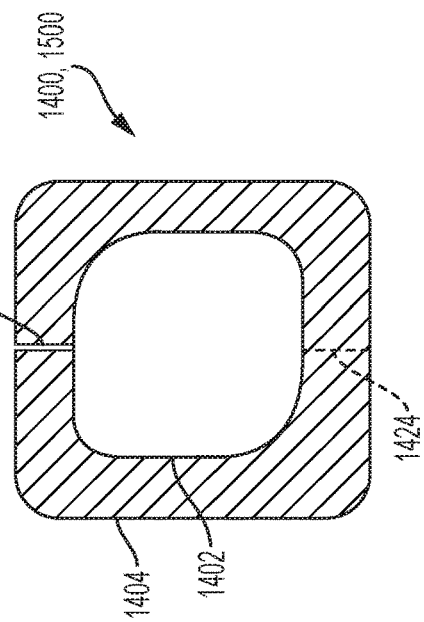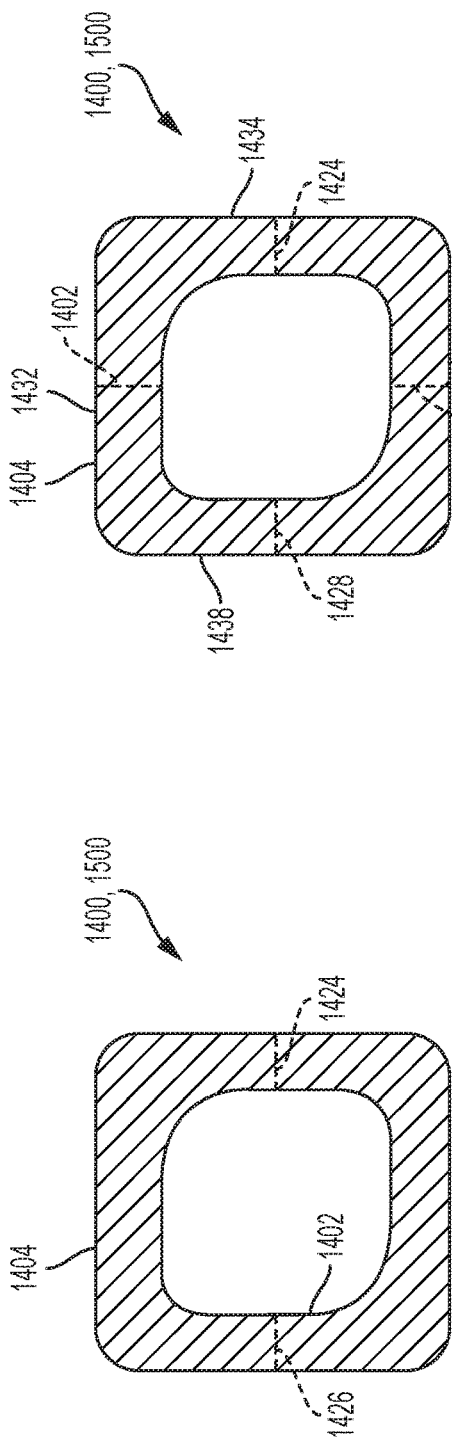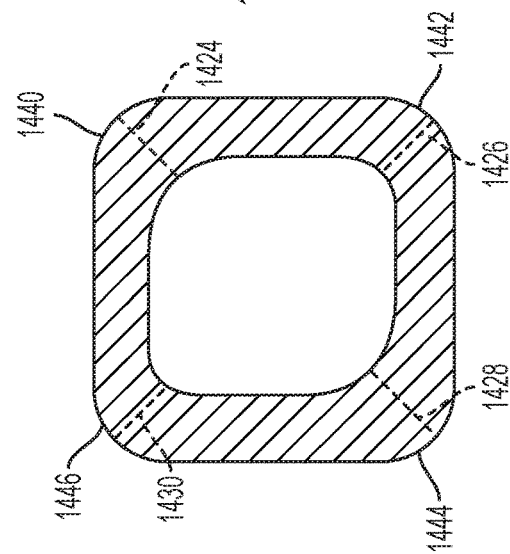

PERFORATED OSTOMY BARRIER EXTENDER

This is a National Stage Application of International Patent Application No. PCT/US2017/030761, filed May 3, 2017, which claims the benefit of and priority to US Provisional Application No. 62/331,119, filed May 3, 2016, the entirety of which are incorporated fully herein by reference.

BACKGROUND

The present disclosure relates to ostomy appliances, and more particularly to extenders for ostomy skin barriers (also known as flanges, wafers, barriers.)

An ostomy appliance is a medical device or prosthetic provided for collecting body waste from a stoma typically created as a result of a surgical procedure to divert a portion of the colon, small intestine, or bladder. One type of ostomy appliance is a pouch that is attached to a user around a stoma.

Typically, a faceplate including an inlet opening to receive a stoma is used to attach an ostomy appliance, such as a pouch, to a user. The faceplate may include an adhesive skin barrier to seal against the user's peristomal skin. Some ostomates use barrier extenders to layer over a portion of the skin barrier edges for added security. Barrier extenders having a curved or semi-circular shaped body are known. For example, a semi-circular shaped skin adhesive tape for layering over an edge of a skin barrier to reduce the risk of leakage and the risk of a faceplate lifting off from user's skin are available in the market.

The present disclosure provides an improved skin barrier extender according to various embodiments.

BRIEF SUMMARY

Ostomy barrier extenders including at least one perforated feature are provided according to various embodiments. The ostomy barrier extender is configured to be divided along the at least one perforated feature by a user. The perforated feature provides versatility by allowing the barrier extender to be delivered to a user as a frame, which may be used to overlay and circumscribe an ostomy skin barrier around its entire periphery when desired, and also allowing the barrier extender to be divided into pieces of different shapes and sizes by separating the barrier extender along perforated features. Thus, a barrier extender according to various embodiments of the present disclosure may be used to provide additional security around its entire periphery or at particular leak-prone areas to prevent edge lifting and/or leakage.

In one aspect, an ostomy barrier extender comprising a skin friendly adhesive layer, a backing layer laminated on one surface of the skin friendly adhesive layer, a release liner laminated on the other surface of the skin friendly adhesive layer, and at least one perforated feature is provided. The ostomy barrier extender further includes an outer periphery, an inner periphery and a ring shaped body defined between the outer periphery and the inner periphery. The ostomy barrier extender is configured to separate along the at least one perforated feature. In an embodiment, the at least one perforated feature may extend through the skin friendly adhesive layer and the backing layer. In other embodiments, the at least one perforated feature may extend through the backing layer, the skin friendly adhesive layer, and the release liner.

In an embodiment, the ostomy barrier extender may include an inner circular periphery and an outer circular periphery to define a circular ring shaped body therebetween, and two perforated lines extending from the inner circular periphery to the outer circular periphery. Each of the two perforated lines may extend in a straight line and may be arranged on the ring shaped body at about 180° from each other, in which the ostomy barrier extender may be configured to divide into two half-ring shaped barrier extenders.

In another embodiment, the ostomy barrier extender may have a ring shaped body including a perforated line and a split defined by a gap between two peripheral ends of the ring shaped body.

In yet another embodiment, the ostomy barrier extender may have a ring shaped body including two perforated lines arranged on the ring shaped body at about 180° from each other, in which a notch may be provide at each end of the perforated lines to facilitate separation of the barrier extender along the perforated lines.

In an embodiment, the ostomy barrier extender may have a ring shaped body including three perforated lines arranged on the circular ring shaped body at about 120° from each other.

In another embodiment, the ostomy barrier extender may have a ring shaped body including four perforated lines arranged on the ring shaped body at about 90° from each other.

In some embodiments, the ostomy barrier extender may include a square inner periphery and a square outer periphery to define a square ring shaped body therebewteen. The corners of the inner periphery and the corners of the outer periphery may be rounded.

The ostomy barrier extender may include two perforated lines arranged on straight leg portions of the square ring shaped body at about 180° from each other. In such an embodiment, the ostomy barrier extender may be configured to divide into two half-square ring shaped barrier extenders by separating the ostomy barrier extender along the two perforated lines. Alternatively, the two perforated lines may be arranged at two corners of the ostomy barrier extender about 180° from each other, in which the ostomy barrier extender is configured to divide into two v-shape barrier extenders by separating the ostomy barrier extender along the two perforated lines. In yet another embodiment, the ostomy barrier extender has a square ring shaped body may include four perforated lines arranged at each of the four corners about 90° from each other. In such an embodiment, the ostomy barrier extender may be configured to divide into four strip-like barrier extenders having slanted peripheral edges by separating the ostomy barrier extender along the four perforated lines.

In an embodiment, the ostomy barrier extender may include a circular inner periphery and a square outer periphery with rounded corners and a ring shaped body defined therebetween. The ostomy barrier extender may include two perforated lines arranged on the body at about 180° from each other, in which the ostomy barrier extender may be configured to divide into two c-shaped barrier extenders by separating the ostomy barrier extender along two perforated lines. In another embodiment, the ostomy barrier extender includes an oval inner periphery and a square outer periphery having rounded corners.

In some embodiments, the ostomy barrier extender may include a circular inner periphery and an oval outer periphery defining an oval ring shaped body therebetween. The ostomy barrier extender may include two perforated lines arranged on the oval ring shaped body at about 180° from each other, in which the ostomy barrier extender may be configured to divide into two c-shaped barrier extenders by separating the ostomy barrier extender along two perforated lines. Further, the ostomy barrier extender may include two curved perforated lines arranged on the oval ring shaped body, such that the oval ring shaped body may be changed to a circular ring shaped body including a circular outer periphery by separating the ostomy barrier extender along the two curved perforated lines.

In an embodiment, the ostomy barrier extender may comprise a plurality of barrier extender strips, in which adjacent barrier extender strips are connected by a perforated line provided along a common periphery.

In another embodiment, the ostomy barrier extender may include four straight perforated lines arranged at about 90° from each other and four curved perforated lines, in which the four curved perforated lines define a circular outline together. The ostomy barrier extender may be configured to separate along the perforated lines to customize a shape and a size of the ostomy barrier extender.

In any of the foregoing embodiments, the skin friendly adhesive layer may comprise hydrocolloid, and the backing layer may be formed from a thin urethane film. Further, the release liner may be provided with a cut line or at least one peel tab to facilitate removal of the release liner.

Other aspects, objectives and advantages will become more apparent from the following detailed description when taken in conjunction with the accompanying drawings.

BRIEF DESCRIPTION OF THE DRAWINGS

The benefits and advantages of the present embodiments will become more readily apparent to those of ordinary skill in the relevant art after reviewing the following detailed description and accompanying drawings, wherein:

FIG. 24 is a perspective view of a barrier extender including two perforated lines according to an embodiment;

FIG. 25 is a perspective view of an oval ring shaped barrier extender including two perforated lines according to an embodiment;

FIG. 26 is a perspective view of an oval ring shaped barrier extender including two curved perforated lines according to another embodiment;

FIG. 27 is a schematic illustration of the oval ring shaped ostomy barrier extender of FIG. 25 used to overlay the circular shaped ostomy skin barrier of FIG. 10 according to an embodiment;

FIG. 28 is a schematic illustration of the oval ring shaped ostomy barrier extender of FIG. 25 used to overlay the oval shaped ostomy skin barrier of FIG. 9 according to an embodiment;

FIG. 29 is a schematic illustration of the oval ring shaped ostomy barrier extender of FIG. 25 used to overlay the triangular shaped ostomy skin barrier of FIG. 11 according to an embodiment;

FIG. 30 is a schematic illustration of the oval ring shaped ostomy barrier extender of FIG. 25 used to overlay the square shaped ostomy skin barrier of FIG. 12 according to an embodiment;

FIG. 31 is a perspective view of barrier extender strips according to an embodiment;

FIGS. 32A-32B are perspective views of barrier extender strips provided in a roll form according to an embodiment;

FIGS. 33A-33B are perspective views of barrier extender strips provided in a folded form according to another embodiment;

FIGS. 34A-34C are perspective views of a barrier extender including eight perforated lines according to an embodiment;

FIG. 43 is a perspective view of a ring shaped barrier extender including four perforated lines extending across respective sides according to an embodiment;

FIG. 44 is a perspective view of a ring shaped barrier extender including four perforated lines extending across respective corners according to an embodiment;

FIG. 45 is a perspective view of a ring shaped barrier extender including a perforated line and a split according to an embodiment;

FIG. 46 is a perspective view of a ring shaped barrier extender having a first width and having a circular opening according to an embodiment;

FIG. 47 is a perspective view of a square ring shaped barrier extender having a second width and having a circular opening according to an embodiment;

FIG. 48 is a schematic illustration of the square ring shaped ostomy barrier extender of FIG. 46 or FIG. 47 used to overlay the square shaped ostomy skin barrier of FIG. 12 according to an embodiment;

FIG. 49 is a schematic illustration of the square ring shaped ostomy barrier extender of FIG. 46 or FIG. 47 used to overlay the triangular shaped ostomy skin barrier of FIG. 11 according to an embodiment;

FIG. 50 is a schematic illustration of the square ring shaped ostomy barrier extender of FIG. 46 or FIG. 47 used to overlay the oval shaped ostomy skin barrier of FIG. 9 according to an embodiment;

FIG. 51 a schematic illustration of the square ring shaped ostomy barrier extender of FIG. 46 or FIG. 47 used to overlay the circular shaped ostomy skin barrier of FIG. 10 according to an embodiment;

FIG. 61 is a perspective view of a square ring shaped barrier extender having an oval opening and including two perforated lines according to an embodiment;

FIG. 62 is a perspective view of a square ring shaped barrier extender having an oval opening and including four perforated lines extending across respective sides according to an embodiment;

FIG. 63 is a perspective view of a square ring shaped barrier extender having an oval opening and including four perforated lines extending across respective corners according to an embodiment;

FIG. 64 is a perspective view of a square ring shaped barrier extender having an oval opening and including a perforated line and a split according to an embodiment;

DETAILED DESCRIPTION

Figure 1:
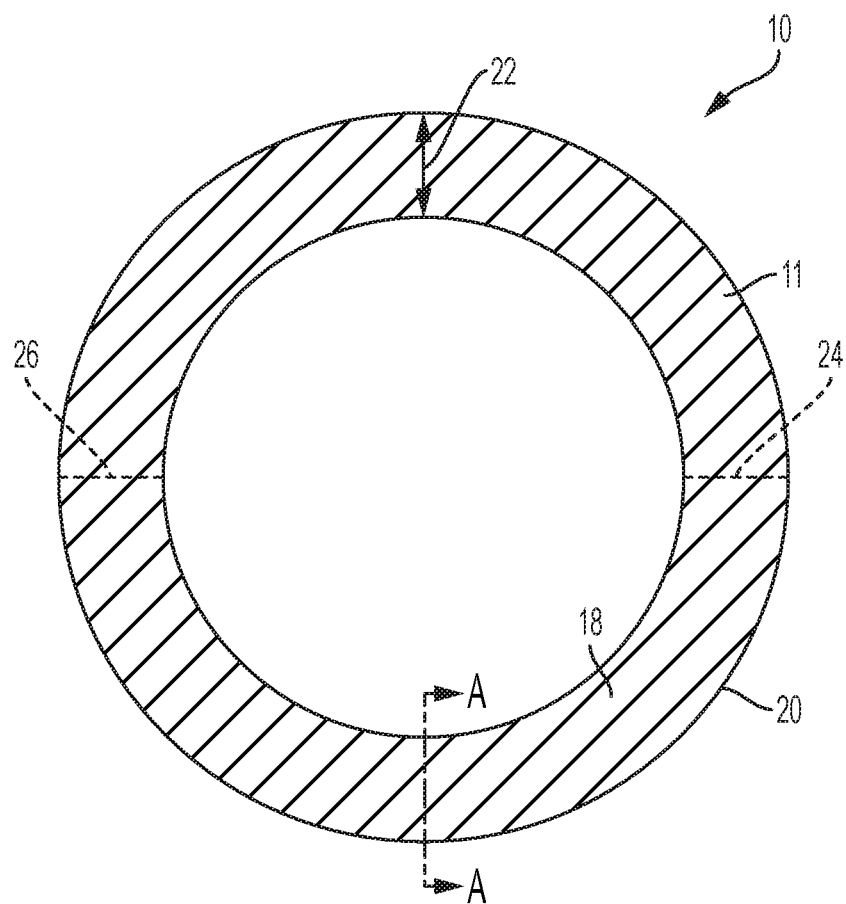
FIG. 1 is a perspective top view of a circular ring shaped ostomy barrier extender including two perforated lines according to an embodiment.

While the present disclosure is susceptible of embodiment in various forms, there is shown in the drawings and will hereinafter be described presently preferred embodiments with the understanding that the present disclosure is to be considered an exemplification and is not intended to limit the disclosure to the specific embodiments illustrated.

Figure 2:
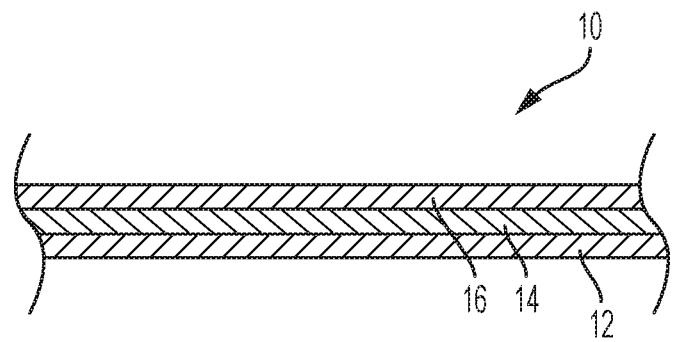
FIG. 2 is a cross sectional view of the barrier extender of FIG. 1.
Figure 3:
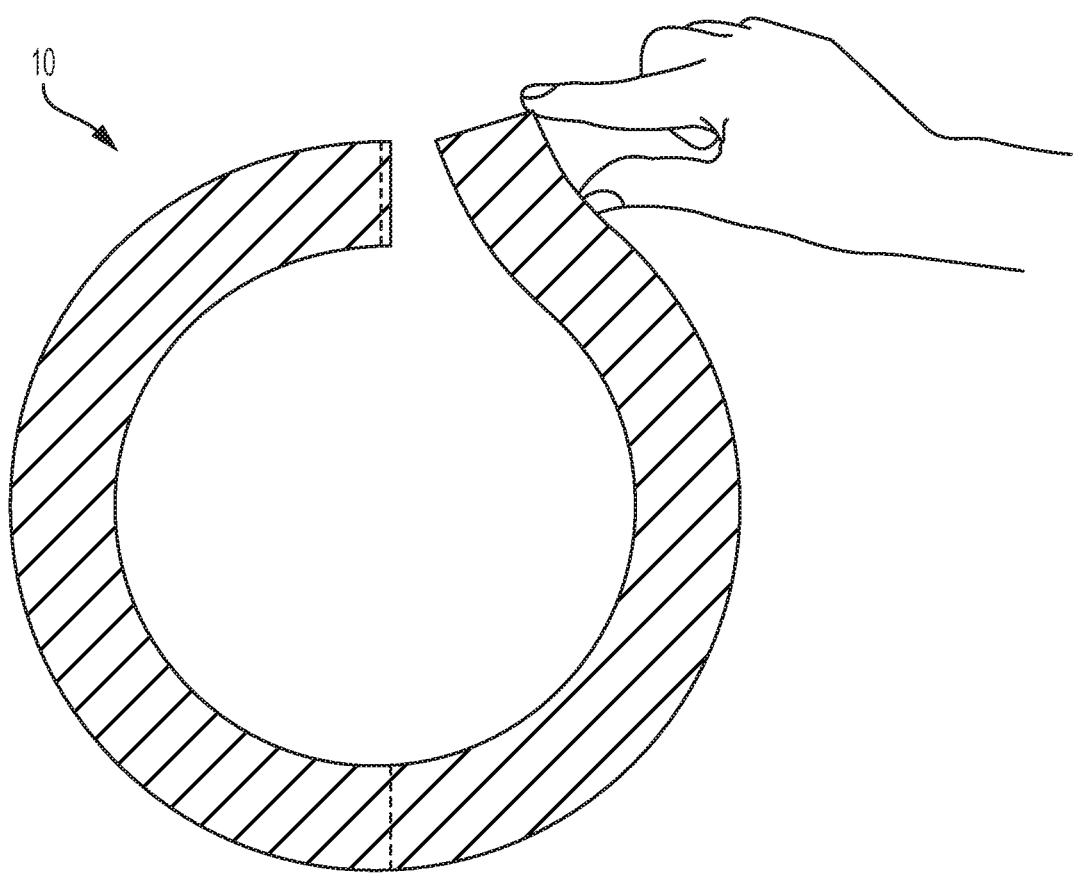
FIG. 3 is a perspective view of the barrier extender of FIG. 1 with a perforated line separated by a user.

Referring to FIGS. 1-3, an embodiment of an ostomy barrier extender 10 for an ostomy appliance according to an embodiment is shown. The barrier extender 10 generally includes a backing layer 12, an adhesive layer 14, and a release liner 16. The barrier extender has a body that may be of various shapes and sizes. In this embodiment, the barrier extender has a circular ring shaped body 11 including an inner circular periphery 18, an outer circular periphery 20, and a width 22 defined therebetween. Further, the barrier extender 10 may include at least one perforated feature, which is configured such that a user may divide at least the backing layer 12 and the adhesive layer 14 of the barrier extender 10 by separating the barrier extender 10 along the at least one perforated feature. The at least one perforated feature may extend through the backing layer 12 and an adhesive layer 14, or through all of the layers including the backing layer 12, the adhesive layer 14, and the release liner 16. In this embodiment, the barrier extender 10 includes two perforated lines 24, 26 extending across the width 22 of the body 11 to facilitate separation of the barrier extender 10 into two pieces as desired by a user. The perforated lines 24, 26 may extend through the backing layer 12 and the adhesive layer 14, or extend through the backing layer 12, the adhesive layer 14, and the release liner 16.

The inner circular periphery 18 and the outer circular periphery 20 of the barrier extender 10 may be concentric circles providing a constant width 22 around the circular ring shaped body 11 of the barrier extender 10. In other embodiments, a barrier extender may have oval shaped inner or outer peripheries, and a width that varies around the body of the barrier extender. Further, in this embodiment, the barrier extender 10 may include two perforated lines 24, 26, which are arranged at about 180° from each other. In other embodiments, two perforated lines may be provided at different locations, for example, 30° or 90° from each other, or the barrier extender may include one perforated line or more than two perforated lines, which may be arranged at various locations on the barrier extender.

The backing layer 12 of the barrier extender 10 may be formed from a suitable material, such as a thin polymeric film. For example, the backing layer 12 may be formed from a thin layer of polyurethane film. The adhesive layer 14 of the barrier extender 10 may be formed from a suitable skin friendly adhesive. For example, the adhesive layer 14 may be formed from a skin barrier material, such as a hydrocolloid formulation, a silicone adhesive or a medical skin grade adhesive. The release liner 16 may be formed from a suitable material that may be easily peeled off from the adhesive layer 14. For example, the release liner 16 may be formed from a silicone coated paper.

Figure 4:
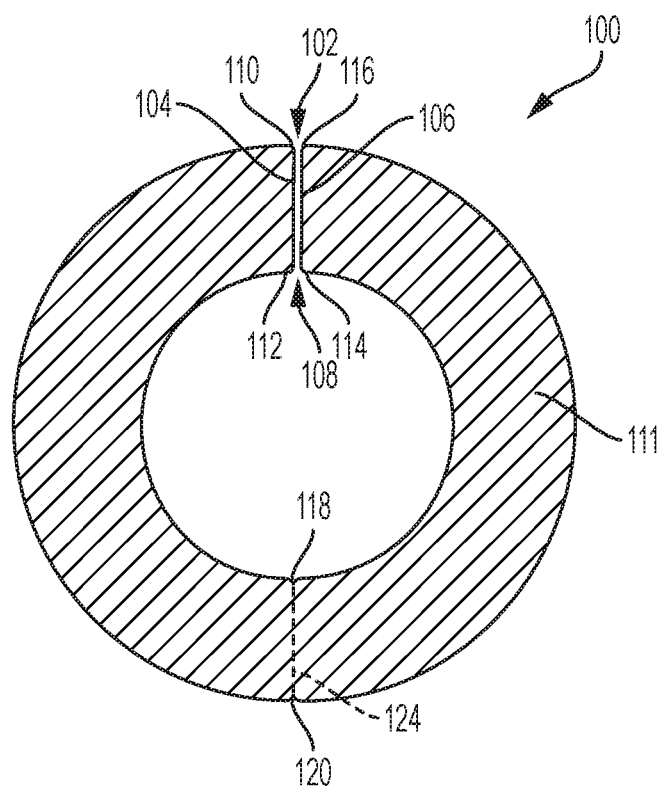
FIG. 4 is a perspective view of a circular ring shaped barrier extender including a perforated line and a split according to an embodiment.

FIG. 4 is an illustration of an ostomy barrier extender 100 according to an embodiment. The barrier extender 100 is constructed similarly to the barrier extender 10 of FIGS. 1-3, and may have a circular ring shaped body 111. The barrier extender 100 includes one perforated line 124 and a split 102 defined by a gap 108 between peripheral edges 104, 106. The corners 110, 112, 114, 116 of the peripheral edges 104, 106 may be rounded. The barrier extender 100 may include notches 118, 120 at one or both ends of the perforated line 124 to facilitate separation of the barrier extender 100 into two pieces.

Figure 5:
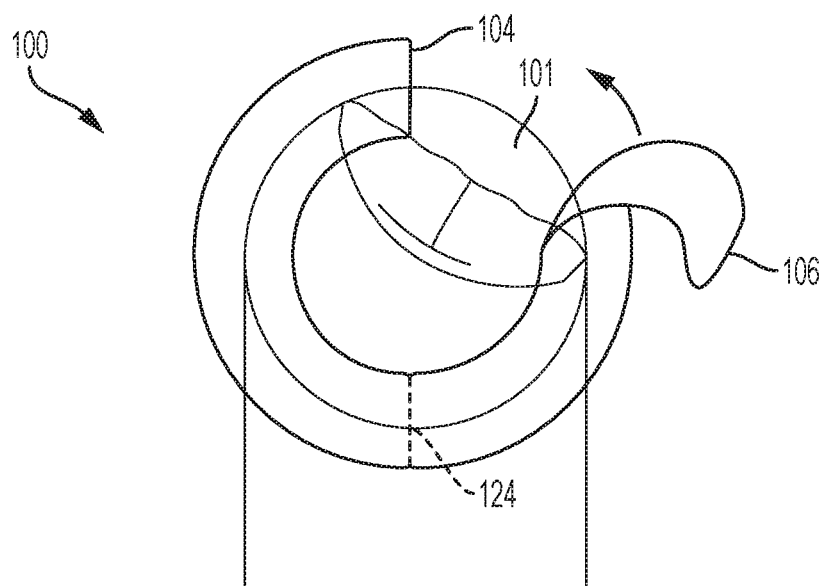
FIG. 5 is a perspective view of the barrier extender of FIG. 4 in use according to an embodiment.

In use, the split 102 may be used to facilitate wrapping and overlaying of the barrier extender 100 around a skin barrier 101 as shown in FIG. 5. Alternatively, the barrier extender 100 may be separated at the perforated line 124 into two arcuate shaped barrier extenders. In this embodiment, the split 102 and the perforated line 124 are arranged at about 180° from each other. In other embodiments, the split 102 and the perforated line 124 may be arranged at various locations on the barrier extender 100, at various angles from each other. In some embodiments, the barrier extender may include one split and more than one perforated lines.

Figure 6:
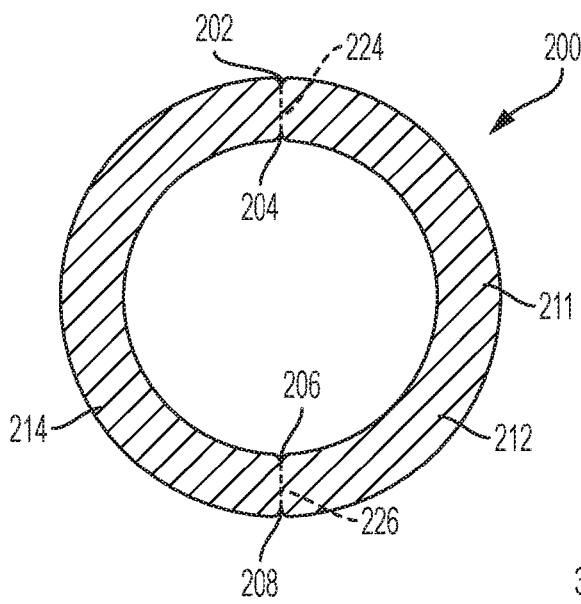
FIG. 6 is a perspective view of a circular ring shaped barrier extender including two perforated lines according to another embodiment.

FIG. 6 is an illustration of an ostomy barrier extender 200 according to another embodiment. The barrier extender 200 may be constructed similarly to the barrier extender 10 of FIGS. 1-3, including a circular ring shaped body 211 and two perforated lines 224, 226, except the barrier extender 200 may include notches 202, 204, 206, 208 at one or both of the ends of the perforated lines 224, 226. In use, a user may separate the barrier extender 200 at one of the two perforated lines 224, 226 to facilitate the use of the barrier extender 200 as a circular ring shaped frame to overlay and circumscribe a skin barrier. Alternatively, the barrier extender 200 may be separated along both perforated lines 224, 226 and divided into two arcuate shaped barrier extenders 212, 214.

Figure 7:
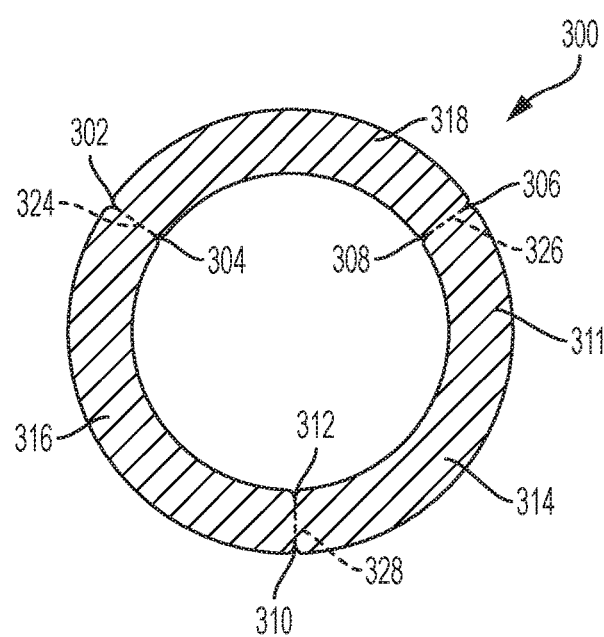
FIG. 7 is a perspective view of a circular ring shaped barrier extender including three perforated lines according to an embodiment.

Referring to FIG. 7, an embodiment of an ostomy barrier extender 300 for an ostomy appliance according to an embodiment is shown. The barrier extender 300 may be constructed similarly to the barrier extender 200 of FIG. 6 having a circular ring shaped body 311, except the barrier extender 300 may include three perforated lines 324, 326, 328. One or both of the ends of the perforated lines 324, 326, 328 may be provided with notches 302, 304, 306, 308, 310, 312 to facilitate separation of the barrier extender 300 into three arcuate shaped barrier extenders 314, 316, 318. In this embodiment, the perforated lines 324, 326, 328 may be arranged at about 120° from each other. In other embodiments, the perforated lines 324, 326, 328 may be arranged at various locations on the circular ring shaped body 311, for example, less than or greater than 120° from each other.

Figure 8:
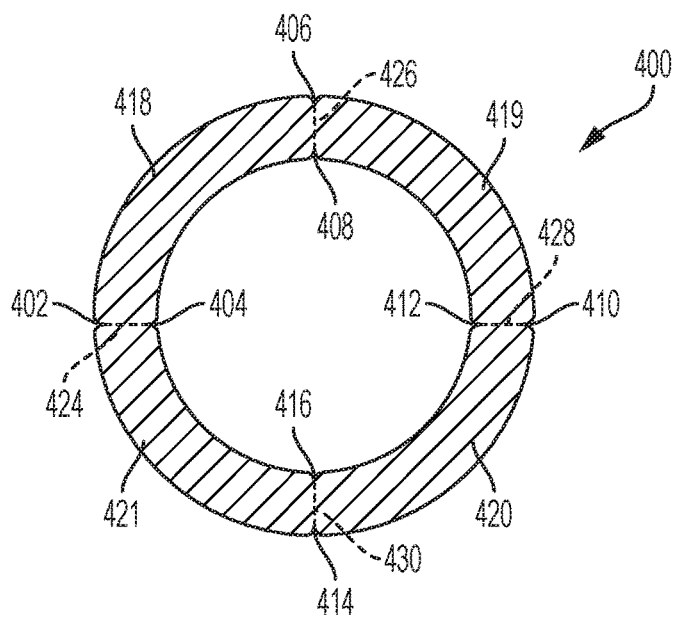
FIG. 8 is a perspective view of a circular ring shaped barrier extender including four perforated lines according to an embodiment.
Figure 9:
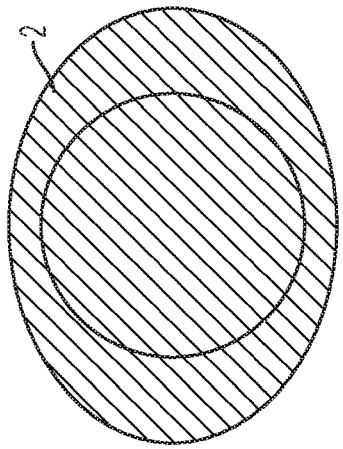
FIG. 9 is a schematic illustration of an oval shaped ostomy skin barrier according to an embodiment.
Figure 10:
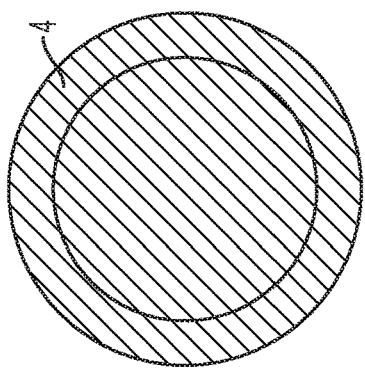
FIG. 10 is a schematic illustration of a circular shaped ostomy skin barrier according to an embodiment.
Figure 11:
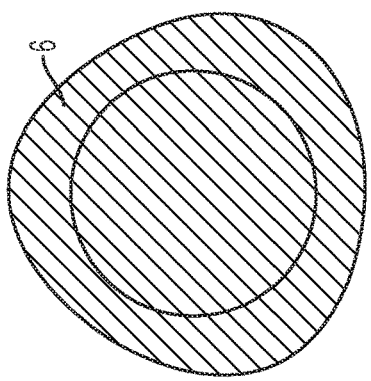
FIG. 11 is a schematic illustration of a triangular shaped ostomy skin barrier according to an embodiment.

FIG. 8 is an illustration of an ostomy barrier extender 400 according to another embodiment. The barrier extender 400 may be constructed similarly to the barrier extender 200 of FIG. 6 having a circular ring shaped body 411, except the barrier extender 400 may include four perforated lines 424, 426, 428, 430. One or both of the ends of the perforated lines 424, 426, 428, 430 may be provided with notches 402, 404, 406, 408, 410, 412, 414, 416 to facilitate separation of the barrier extender 400 into four arcuate shaped barrier extenders 418, 419, 420, 421. In this embodiment, the perforated lines 424, 426, 428, 430 are arranged at about 90° from each other. In other embodiments, the perforated lines 424, 426, 428, 430 may be arranged at various locations on the circular ring shaped body 411, for example, less than or greater than 90° from each other.

Figure 12:
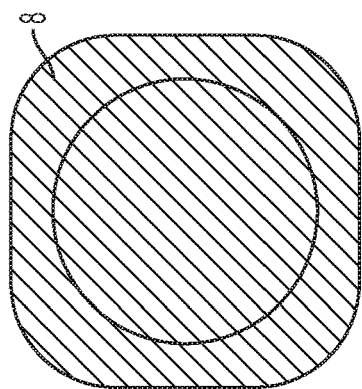
FIG. 12 is a schematic illustration of a square shaped ostomy skin barrier according to an embodiment.
Figure 13:
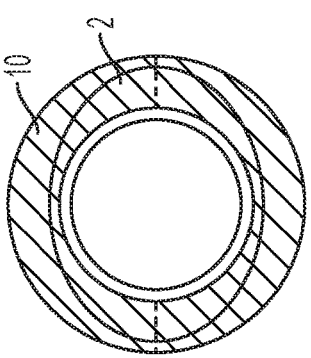
FIG. 13 is a schematic illustration of the circular ring shaped ostomy barrier extender of FIG. 1 used to overlay the oval shaped ostomy skin barrier of FIG. 9 according to an embodiment.
Figure 14:
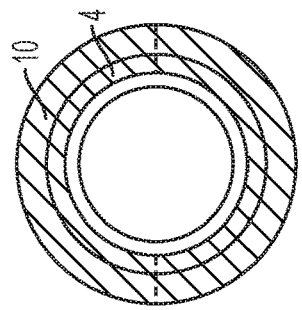
FIG. 14 is a schematic illustration of the circular ring shaped ostomy barrier extender of FIG. 1 used to overlay the circular shaped ostomy skin barrier of FIG. 10 according to an embodiment.
Figure 15:
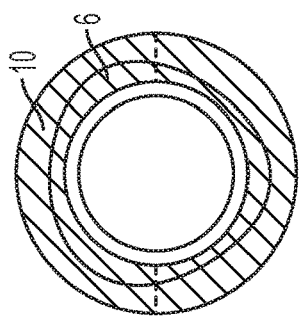
FIG. 15 is a schematic illustration of the circular ring shaped ostomy barrier extender of FIG. 1 used to overlay the triangular shaped ostomy skin barrier of FIG. 11 according to an embodiment.
Figure 16:
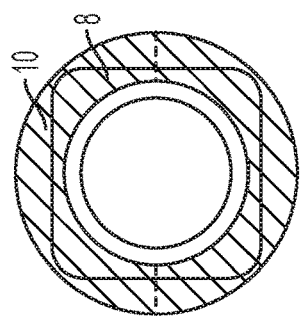
FIG. 16 is a schematic illustration of the circular ring shaped ostomy barrier extender of FIG. 1 used to overlay the square shaped ostomy skin barrier of FIG. 12 according to an embodiment.

FIGS. 9-12 illustrate ostomy skin barriers of various shapes: an oval shaped skin barrier 2 (FIG. 9), a circular shaped skin barrier 4 (FIG. 10), a triangular shaped skin barrier 6 (FIG. 11), and a square shaped skin barrier 8 (FIG. 12). A circular ring shaped ostomy barrier extender including at least one perforated feature, such as the ostomy barrier extender 10, 100, 200, 300, 400 of the forgoing embodiments may be used to overlay and frame around an ostomy skin barrier of various shapes. For example, the ostomy barrier extender 10 may be used to overlay and frame around the oval shaped skin barrier 2, the circular shaped skin barrier 4, the triangular shaped skin barrier 6, and the square shaped skin barrier 10 as shown in FIGS. 13-16.

Figure 19:
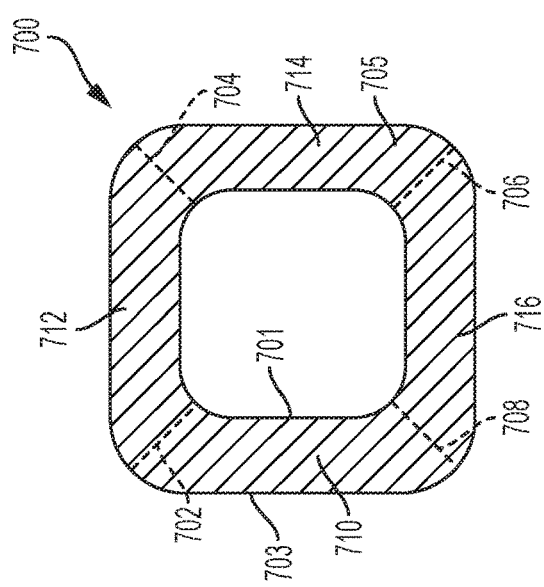
FIG. 19 is a perspective view of a square ring shaped barrier extender including four perforated lines according to an embodiment.
Figure 18:
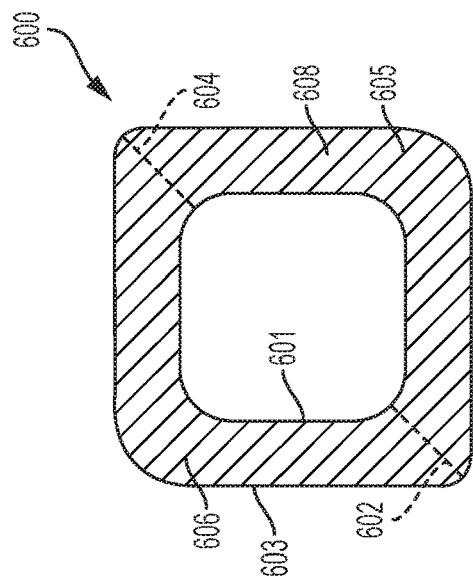
FIG. 18 is a perspective view of a square ring shaped barrier extender including two perforated lines according to another embodiment.
Figure 17:
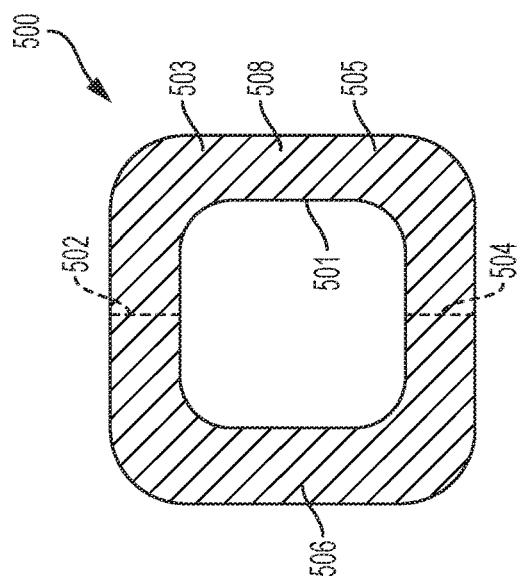
FIG. 17 is a perspective view of a square ring shaped barrier extender including two perforated lines according to an embodiment.
Figure 23:
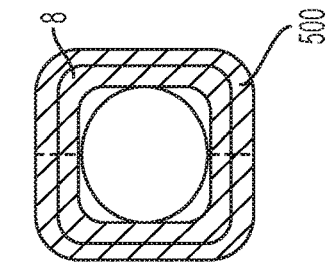
FIG. 23 is a schematic illustration of the square ring shaped ostomy barrier extender of FIG. 17 used to overlay the square shaped ostomy skin barrier of FIG. 12 according to an embodiment.
Figure 22:
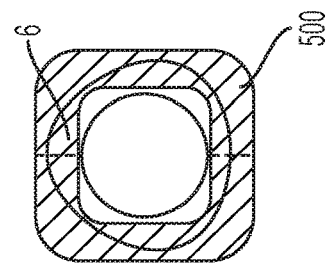
FIG. 22 is a schematic illustration of the square ring shaped ostomy barrier extender of FIG. 17 used to overlay the triangular shaped ostomy skin barrier of FIG. 11 according to an embodiment.
Figure 21:
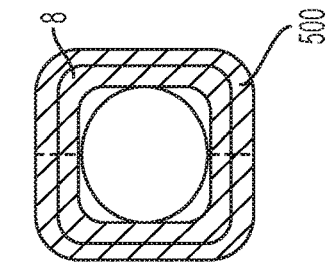
FIG. 21 is a schematic illustration of the square ring shaped ostomy barrier extender of FIG. 17 used to overlay the oval shaped ostomy skin barrier of FIG. 9 according to an embodiment.
Figure 20:
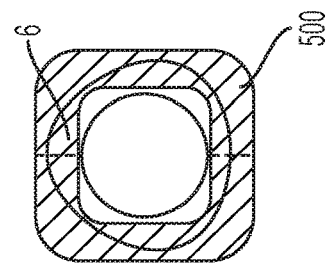
FIG. 20 is a schematic illustration of the square ring shaped ostomy barrier extender of FIG. 17 used to overlay the circular shaped ostomy skin barrier of FIG. 10 according to an embodiment.

Referring to FIGS. 17-19, ostomy barrier extenders 500, 600, 700 having a square ring shaped body according to various embodiments are shown. As it was with the foregoing ostomy barrier extender embodiments 10, 100, 200, 300, 400, each of the ostomy barrier extenders 500, 600, 700 may generally include a backing layer, an adhesion layer, a release liner, and at least one perforated feature. As shown in FIGS. 17-19, each of the barrier extenders 500, 600, 700 may include a generally square inner periphery 501, 601, 701 and a generally square outer periphery 503, 603, 703 defining a square ring shaped body 505, 605, 705 therebetween. Corners of the inner and outer peripheries may be rounded.

The ostomy barrier extender 500 of FIG. 17 may include two perforated lines 502, 504 for facilitating separation of the barrier extender 500 into two pieces. As shown in FIG. 17, each of the perforated lines 502, 504 may be arranged on a straight leg portion of the square ring shaped body between two corners at about 180° from each other, such that the ostomy barrier extender 500 may be divided into two barrier extenders 506, 508 having a half-rounded square shaped body.

Similarly, the ostomy barrier extender 600 of FIG. 18 may include two perforated lines 602, 604. As shown in FIG. 18, each of the perforated lines 602, 604 may be arranged at diagonal corners of the square ring shaped body, about 180° from each other, such that the barrier extender 600 may be divided into two barrier extenders 606, 608 having a rounded v-shaped body.

The ostomy barrier extender 700 may include four perforated lines 702, 704, 706, 708. As shown in FIG. 19, each of the perforated lines 702, 704, 706, 708 may be arranged at each corner of the square ring shaped body about 90° from each other, such that the barrier extender 700 may be divided into four barrier extenders 710, 712, 714, 716 having a strip-like shaped body with slanted ends.

A square ring shaped ostomy barrier extender including at least one perforated feature, such as the ostomy barrier extender 500, 600, 700 of FIGS. 17-19 may be used to overlay and frame around ostomy skin barriers of various shapes. For example, the ostomy barrier extender 500 may be used to overlay and frame around the circular shaped skin barrier 4, the oval shaped skin barrier 2, the triangular shaped skin barrier 6, and the square shaped skin barrier 10 as shown in FIGS. 20-23.

FIG. 24 illustrates an ostomy barrier extender 800 according to another embodiment. The barrier extender 800 may include a circular inner periphery 802 and a square outer periphery 804 defining a body 803 therebetween, and two perforated lines 814, 816 arrange on straight leg portions of the body 803 at about 180° from each other. The corners 806, 808, 810, 812 of the barrier extender 800 may be rounded with a larger radius than the corners of the barrier extender 500 of FIG. 17, which may further reduce a risk of skin barrier edge lifting.

Referring to FIGS. 25 and 26, ostomy barrier extenders 900, 950 having an oval ring shaped body according to embodiments are shown. The ostomy barrier extenders 900, 950 may include a circular inner periphery 902, 952 and an oval outer periphery 904, 954 defining an oval ring shaped body 903, 953 therebetween. The oval ring shaped barrier extenders 900, 952 may provide additional protection at 3 o'clock and 9 o'clock positions of a skin barrier.

The ostomy barrier extender 900 as shown in FIG. 25 may include two perforated lines 906, 908 arranged on narrower portions of the oval shaped body 903 at about 180° from each other. When separated along the perforated lines 906, 908, the ostomy barrier extender 900 may divide into two c-shaped barrier extenders. In other embodiment, the barrier extender 900 may include more than two perforated lines, and the perforated lines may be arranged at various locations on the ostomy barrier extender 900.

As shown in FIG. 26, the ostomy barrier extender 950 may include two curved perforated lines 956, 958 arranged such that the oval ring shaped barrier extender 950 may be used as a circular ring shaped barrier extender after removing outer peripheral portions by separating the barrier extender 950 along the perforated lines 956, 958.

An oval ring shaped ostomy barrier extender including at least one perforated feature, such as the ostomy barrier extender 900, 950 of FIGS. 25 and 26, may be used to overlay and frame around an ostomy skin barrier of various shapes. For example, the ostomy barrier extender 900 may be used to overlay and frame around the circular shaped skin barrier 4, the oval shaped skin barrier 2, the triangular shaped skin barrier 6, and the square shaped skin barrier 10 as shown in FIGS. 27-30.

Referring to FIGS. 31-33B, ostomy barrier extender strips 750, 760, 770 according to various embodiments are shown. As it was with the foregoing barrier extender embodiments, each of the ostomy barrier extender strips 750, 760, 770 may generally include a backing layer, an adhesion layer, a release liner, and at least one perforated feature.

As shown in FIG. 31, the barrier extender strip 750 is connected to an adjacent barrier extender strip 752 via a perforated line 751 extending lengthwise along a common periphery between the barrier extender strip 750 and the barrier extender strip 752. In this embodiment, a barrier extender 758 includes four barrier extender strips 750, 752, 754, 756 and a perforation line 751, 753, 755 between adjacent barrier strips. In other embodiments, a barrier extender may include less than four or more than four barrier extender strips connected via perforation lines.

FIGS. 32A and 33A illustrate a barrier extender strip 760, 770, which is connected to adjacent barrier extender strips 762, 764, 772, 774 via perforation lines 761, 763, 771, 773 extending widthwise along a common periphery between adjacent barrier extender strips. The barrier extender strip 760 may be provided in a roll form as shown in FIG. 32B or in a folded form as shown in FIG. 33B.

FIGS. 34A-34C illustrate an ostomy barrier extender 850 according to an embodiment. The barrier extender 850 may include a circular inner periphery 852 and a square outer periphery 854 defining a body 853 therebetween. The corners 856, 858, 860, 862 of the barrier extender 850 may be rounded. The barrier extender 850 may comprise eight perforated lines including four straight perforated lines 864, 866, 868, 870 arranged on straight leg portions of the body 853 at about 90° from each other, and four curved perforated lines 872, 874, 876, 878, each of which extend from an outer periphery proximate a straight perforated line to an outer periphery proximate an adjacent straight perforated line, such that the four curved perforated lines 872, 874, 876, 878 form a circular outline together.

The barrier extender 850 is configured to allow a user to choose and change the shape of the barrier extender according to need. For example, a user may remove outer peripheral portions of the barrier extender 850 by separating the barrier extender 850 along two curved perforated lines 872, 876, and use the remaining barrier extender to provide added security around 3 o'clock and 9 o'clock positions of an ostomy skin barrier as shown in FIG. 34C. Alternatively, a user may choose to separate the barrier extender 850 along all four curved perforated lines 872, 874, 876, 878 to make a circular ring shaped barrier extender. The plurality of perforated lines allows a user to customize the shape and size of a barrier extender according to need.

Figure 35B:
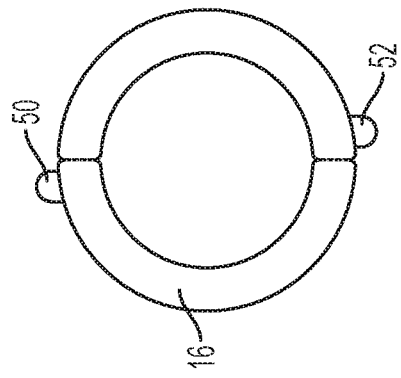
FIGS. 35A-35B are partial schematic views of a barrier extender including a curved cut line provided on a release liner according to an embodiment.
Figure 35A:
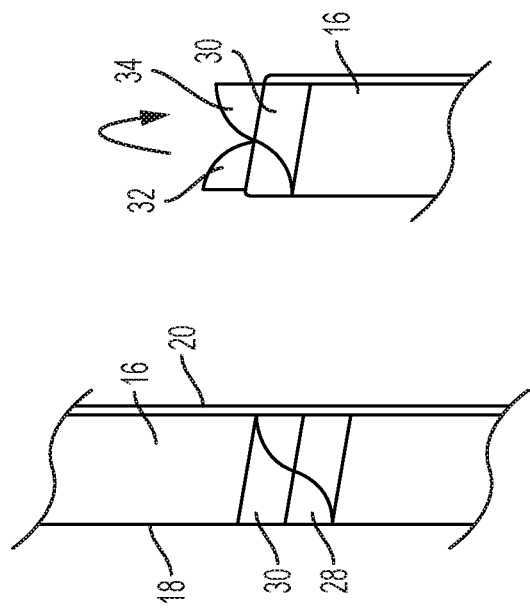

An ostomy barrier extender according to any of the foregoing embodiments may be provided with a means to facilitate removal of a release liner. For example, the ostomy barrier extender 10 of FIGS. 1-3 may be provided with a curved cut line 28 having a slanted S shape on the release liner 16 extending from the inner periphery 18 to the outer periphery 20 as shown in FIG. 35A. The area of the release liner 16 proximate the curved cut line 28 may be provided in a different color than the rest of the release liner 16 for easy identification of the curved cut line 28. The curved cut line 28 is configured such that when the barrier extender 10 is folded about a center line 30 as shown in FIG. 35B, two peel tabs 32, 34 may be provided by the release liner 16 to facilitate removal of the release liner 16.

Figure 37B:
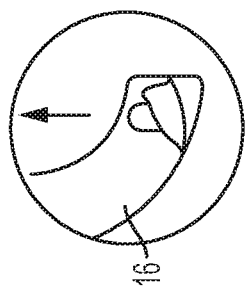
FIGS. 37A-37B are schematic views of a barrier extender including peel tabs provided on a release liner according to yet another embodiment.
Figure 37A:
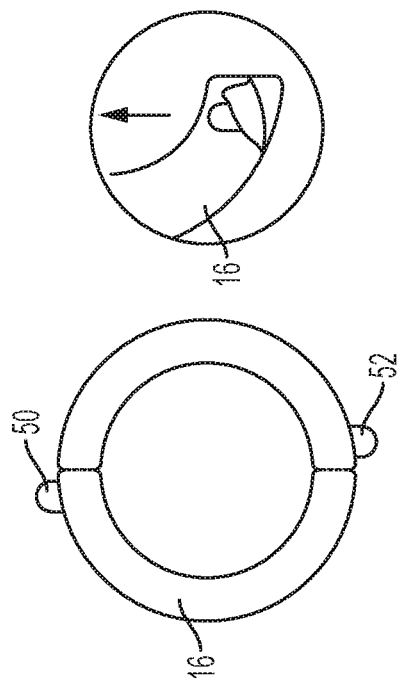
Figure 36:
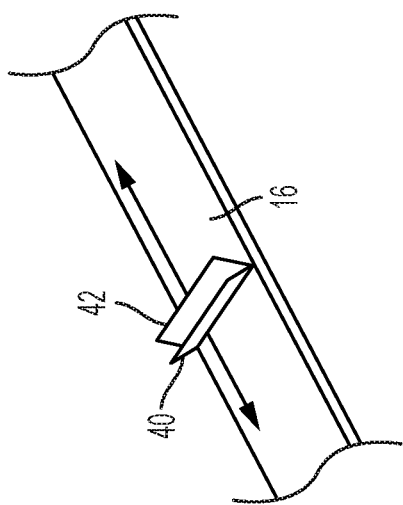
FIG. 36 is a partial schematic view of a barrier extender including folded peel tabs provided on a release liner according to another embodiment.

In another embodiment, a barrier extender may be provided with folded peel tabs 40, 42, which protrude away from the surface of a release liner 16 as shown in FIG. 36. At least some portion of the peel tabs 40, 42 may be colored with a different color than the rest of the release liner 16 for easy identification. In yet another embodiment, a barrier extender may be provided with peel tabs 50, 52, which extend beyond an outer periphery of a release liner 16 to facilitate removal of the release liner 16 as shown in FIGS. 37A and 37B. At least some portion of the peel tabs 50, 52 may be colored in a different color than the rest of the release liner 16.

Figure 39:
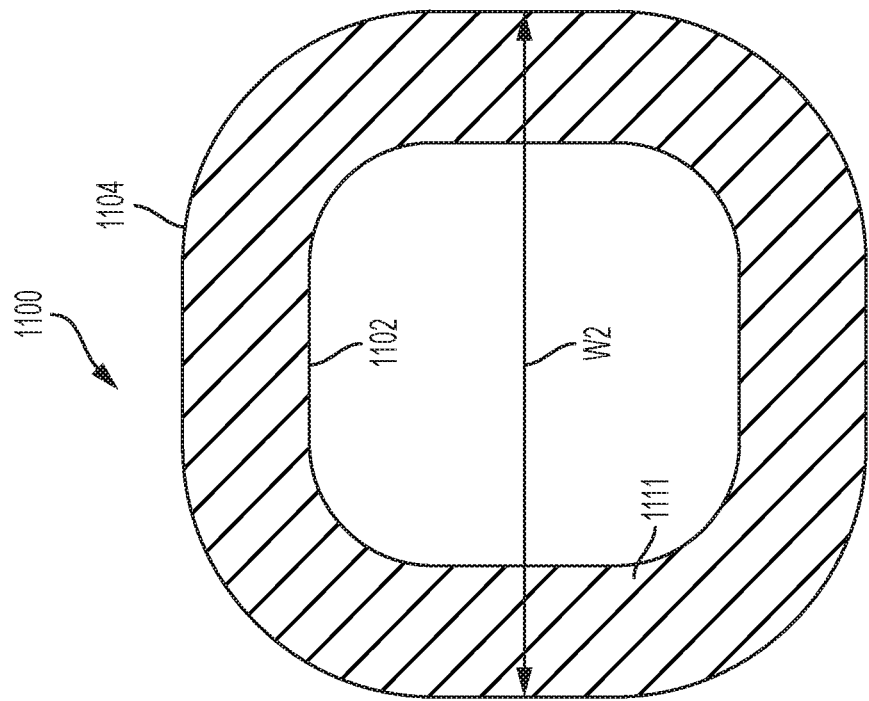
FIG. 39 is a perspective view of a ring shaped barrier extender having a second width, a square inner periphery and a square outer periphery according to an embodiment.
Figure 38:
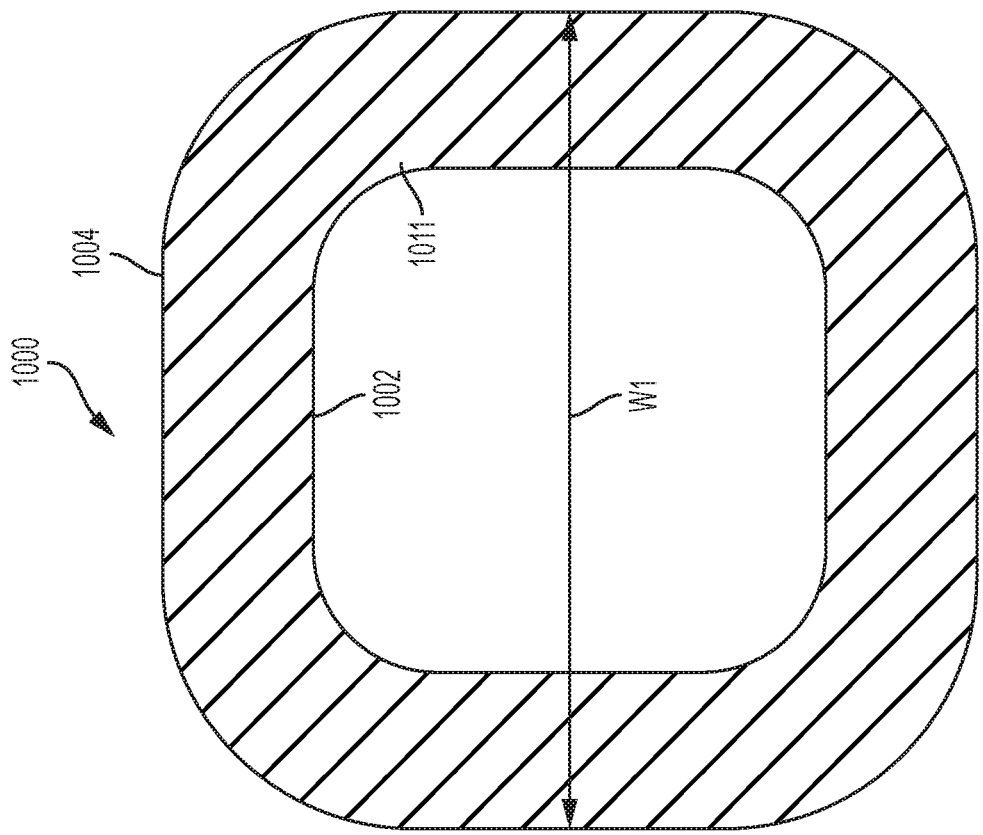
FIG. 38 is a perspective view of a ring shaped barrier extender having a first width, a square inner periphery and a square outer periphery, according to an embodiment.

FIGS. 38 and 39 show differently sized barrier extenders 1000, 1100, according to an embodiment described herein. In the embodiments shown in FIGS. 38 and 39, the barrier extenders are shown as blanks, or non-perforated. Referring to FIG. 38, in one embodiment, the barrier extender 1000 has a generally square inner periphery 1002, a generally square outer periphery 1004, and a ring shaped body 1011 defined therebetween. The barrier extender 1000 has a first width W1. In one embodiment, the first width W1 may be about 6.5 inches, but is not limited thereto. Corners of the square peripheries may be rounded.

Referring to FIG. 39, in one embodiment, the barrier extender 1100 has a generally square inner periphery 1102, a generally square outer periphery 1104, and a ring shaped body 1111 defined therebetween. The barrier extender 1100 has a second width W2. In one embodiment, the second width W2 may be about 5.5 inches, but is not limited thereto. Thus, the barrier extenders 1000, 1100 shown in FIGS. 38 and 39 may be manufactured having different sizes. As such, in the embodiments described herein, the barrier extender may be manufactured in different sizes to overlay differently sized or shaped ostomy skin barriers.

Figure 40:
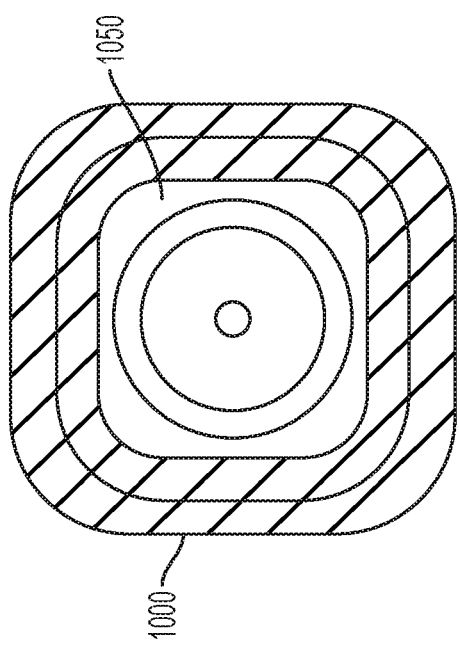
FIG. 40 is a schematic illustration of the ring shaped ostomy barrier extender of FIG. 38 used to overlay a square shaped ostomy skin barrier having a first width according to an embodiment.
Figure 42:
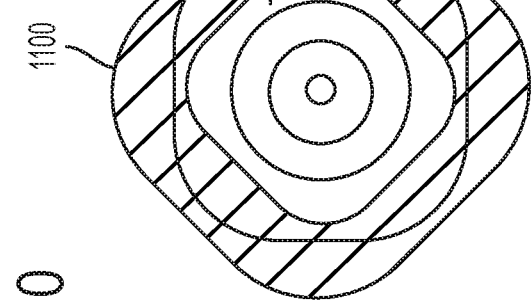
FIG. 42 is a schematic illustration of the ring shaped ostomy barrier extender of FIG. 39 used to overlay a square shaped ostomy skin barrier having a second width according to an embodiment.
Figure 41:
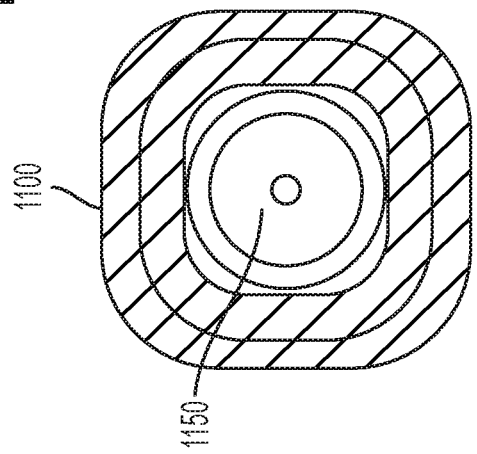
FIG. 41 is a schematic illustration of the ring shaped ostomy barrier extender of FIG. 39 used to overlay a square shaped ostomy skin barrier having a second width according to an embodiment.

FIG. 40 is a schematic illustration of the ring shaped ostomy barrier extender 1000 of FIG. 38 overlaying a square shaped ostomy skin barrier 1050 having a first size according to an embodiment. FIG. 41 is a schematic illustration of the ring shaped ostomy barrier extender 1100 of FIG. 39 overlaying a square shaped ostomy skin barrier 1150 having a second size, less than the first size, according to an embodiment. In FIG. 42, the barrier extender 1100 is applied at a rotationally offset angle relative to the ostomy skin barrier 1150. For example, in one embodiment, the barrier extender 1100 is rotated approximately 45 degrees relative to the skin barrier 1150.

FIGS. 43-45 show examples of different perforation lines that may be formed in the ostomy barrier extender 1000, 1100, according to embodiments described herein. For example, as shown in FIGS. 43 and 44, the ostomy barrier extender 1000, 1100 may include four perforated lines 1024, 1026, 1028, 1030. The perforated lines 1024, 1026, 1028, 1030 may extend from the inner periphery 1002, 1102 to the outer periphery 1004, 1104. Referring to FIG. 43, in one embodiment, the perforated lines 1024, 1026, 1028, 1030 may be formed on respective sides 1032, 1034, 1036, 1038 of the ostomy barrier extender 1000, 1100. In another embodiment, as shown in FIG. 44, the perforated lines 1024, 1026, 1028, 1030 may be formed on respective corners 1040, 1042, 1044, 1046. In other embodiments, the perforated lines may be formed at various combinations of the sides and corners.

Referring to FIG. 45, in one embodiment, the ostomy barrier extender 1000, 1100 includes a perforated line 1024 and a split 1048 defined by a gap extending between the inner periphery 1002 and the outer periphery 1004. In one embodiment, the split 1048 and the perforated line 1024 may be positioned approximately 180 degrees from one another, but the present disclosure is not limited such relative positioning. Further, in one embodiment, the split 1048 and the perforated line 1024 may be formed on opposite sides of the ostomy barrier extender 1000, 1100. However, it is understood that the split 1048 and the perforated line 1024 may be formed on the same side, adjacent sides, opposing corners, adjacent corners or on combinations of the sides and corners.

It is understood that although the perforated lines in FIGS. 43-45 are shown with respect to ostomy barrier extenders 1000, 1100 having substantially square outer peripheries and substantially square inner peripheries, the perforated lines may be used on any of the other barrier extenders described herein. It is also understood that additional or fewer perforated lines may be used, and the locations of the perforated lines may vary.

FIGS. 46 and 47 show differently sized barrier extenders 1200, 1300, according to an embodiment described herein. In the embodiments shown in FIGS. 46 and 47, the barrier extenders are shown as blanks, or non-perforated. Referring to FIG. 46, in one embodiment, the barrier extender 1200 has a generally circular inner periphery 1202, a generally square outer periphery 1204, and a ring shaped body 1211 defined therebetween. The barrier extender 1200 has a first width W1. In one embodiment, the first width W1 may be about 6.5 inches, but is not limited thereto.

Referring to FIG. 47, in one embodiment, the barrier extender 1300 has a generally circular inner periphery 1302, a generally square outer periphery 1304, and a ring shaped body 1311 defined therebetween. The barrier extender 1300 has a second width W2. In one embodiment, the second width W2 may be about 5.5 inches, but is not limited thereto. Thus, the barrier extenders 1200, 1300 shown in FIGS. 46 and 47 may be manufactured having different sizes. As such, in the embodiments described herein, the barrier extender may be manufactured in different sizes to overlay differently sized or shaped ostomy skin barriers.

FIGS. 48-51 are schematic illustrations showing examples of the ostomy barrier extender 1200 (or 1300) overlaying different ostomy skin barriers, according to embodiments described herein. For example, FIG. 48 shows the ostomy barrier extender 1200 overlaying the square shaped ostomy skin barrier 8 of FIG. 12. FIG. 49 shows the ostomy barrier extender 1200 overlaying the triangular shaped ostomy skin barrier 6 of FIG. 11. FIG. 50 shows the ostomy barrier extender 1200 overlaying the oval shaped ostomy skin barrier 2 of FIG. 9. FIG. 51 shows the ostomy barrier extender 1200 overlaying the circular shaped ostomy skin barrier 4 of FIG. 10. In some embodiments, as shown in FIG. 50, for example, the ostomy barrier extender 1200 may be rotated relative to the ostomy skin barrier before application, to extend coverage over various portions of the ostomy skin barrier depending on a shape of the ostomy skin barrier. It is understood that ostomy barrier extender 1300 may overlay ostomy skin barriers in a similar manner.

Figure 52:
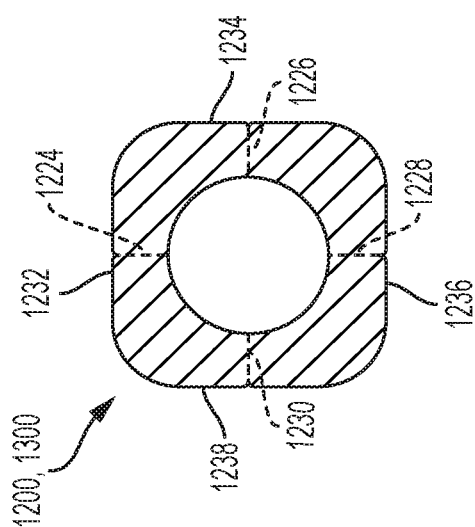
FIG. 52 is a perspective view of a square ring shaped barrier extender having a circular opening and including four perforated lines extending across respective sides according to an embodiment.
Figure 53:
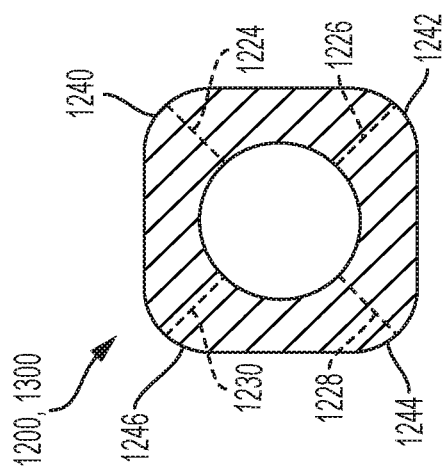
FIG. 53 is a perspective view of a square ring shaped barrier extender having a circular opening and including four perforated lines extending across respective corner according to an embodiment.
Figure 54:
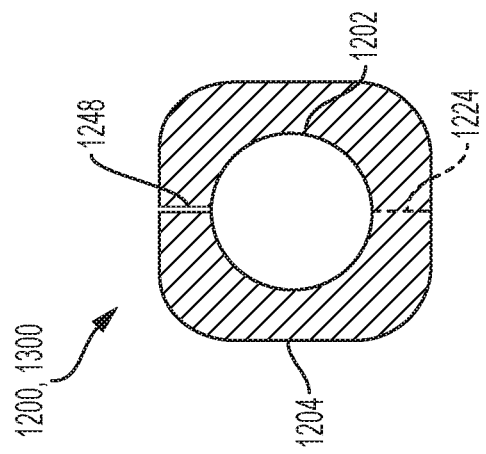
FIG. 54 is a perspective view of a square ring shaped barrier extender having a circular opening and including a perforated line and a split according to an embodiment.

FIGS. 52-54 show examples of different perforation lines that may be formed in the ostomy barrier extender 1200, 1300, according to embodiments described herein. For example, as shown in FIGS. 52 and 53, the ostomy barrier extender 1200, 1300 may include four perforated lines 1224, 1226, 1228, 1230. The perforated lines 1224, 1226, 1228, 1230 may extend from the inner periphery 1202, 1302 to the outer periphery 1204, 1304. Referring to FIG. 52, in one embodiment, the perforated lines 1224, 1226, 1228, 1230 may be formed on respective sides 1232, 1234, 1236, 1238 of the ostomy barrier extender 1200, 1300. In another embodiment, as shown in FIG. 53, the perforated lines 1224, 1226, 1228, 1230 may be formed on respective corners 1240, 1242, 1244, 1246. In other embodiments, the perforated lines may be formed at various combinations of the sides and corners.

Referring to FIG. 54, in one embodiment, the ostomy barrier extender 1200, 1300 includes a perforated line 1224 and a split 1248 defined by a gap extending between the inner periphery 1202 and the outer periphery 1204. In one embodiment, the split 1248 and the perforated line 1224 may be positioned approximately 180 degrees from one another, but the present disclosure is not limited such relative positioning. Further, in one embodiment, the split 1248 and the perforated line 1224 may be formed on opposite sides of the ostomy barrier extender 1200, 1300. However, it is understood that the split 1248 and the perforated line 1224 may be formed on the same side, adjacent sides, opposing corners, adjacent corners or on combinations of the sides and corners.

Figure 55:
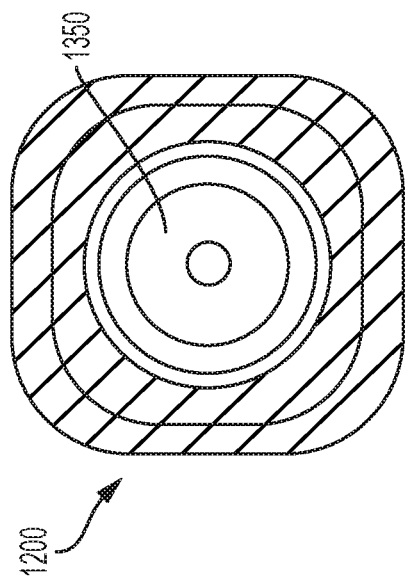
FIG. 55 is a schematic illustration of the square ring shaped ostomy barrier extender having a circular opening of FIG. 46 used to overlay a square shaped ostomy skin barrier having a first width according to an embodiment.
Figure 58:
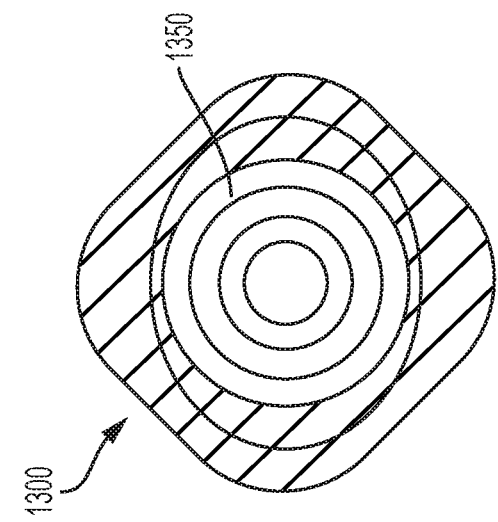
FIG. 58 is a schematic illustration of the square ring shaped ostomy barrier extender having a circular opening of FIG. 47 used to overlay an oval shaped ostomy skin barrier according to an embodiment.
Figure 57:
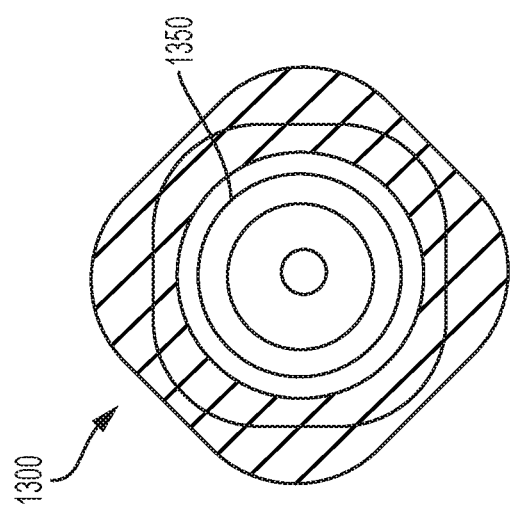
FIG. 57 is a schematic illustration of the square ring shaped ostomy barrier extender having a circular opening of FIG. 47 used to overlay a square shaped ostomy skin barrier having a second width according to an embodiment.
Figure 56:
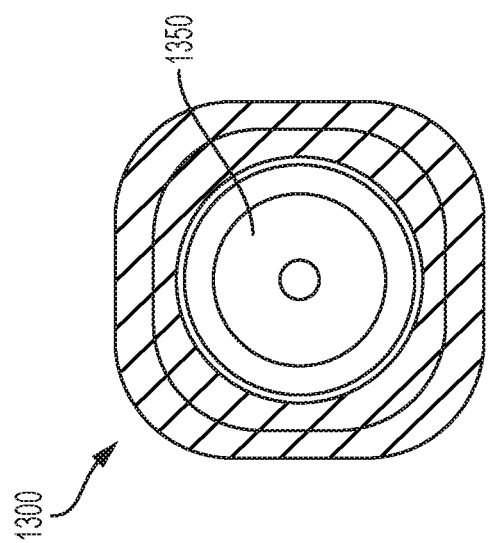
FIG. 56 is a schematic illustration of the square ring shaped ostomy barrier extender having a circular opening of FIG. 47 used to overlay a square shaped ostomy skin barrier having a second width according to an embodiment.

FIG. 55 is a schematic illustration of the ring shaped ostomy barrier extender 1200 having a circular inner periphery of FIG. 46 overlaying a square shaped ostomy skin barrier 1250 having a first size according to an embodiment. FIG. 56 is a schematic illustration of the ring shaped ostomy barrier extender 1300 having a circular inner periphery of FIG. 47 overlaying a square shaped ostomy skin barrier 1350 having a second size, less than the first size, according to an embodiment. FIG. 57 is a schematic illustration of the ring shaped ostomy barrier extender 1300 having a circular inner periphery of FIG. 47 overlaying a square shaped ostomy skin barrier 1350 according to an embodiment. In FIG. 57, the ostomy barrier extender 1300 is applied at a rotational angle different from that shown in FIG. 56. In FIG. 58, the barrier extender 1300 is also applied at a rotationally offset angle. For example, in one embodiment, the barrier extender 1300 is rotated approximately 45 degrees relative to the skin barrier 1350. In addition, in the embodiment of FIG. 58, the ostomy skin barrier 1350 may be oval in shape.

Figure 60:
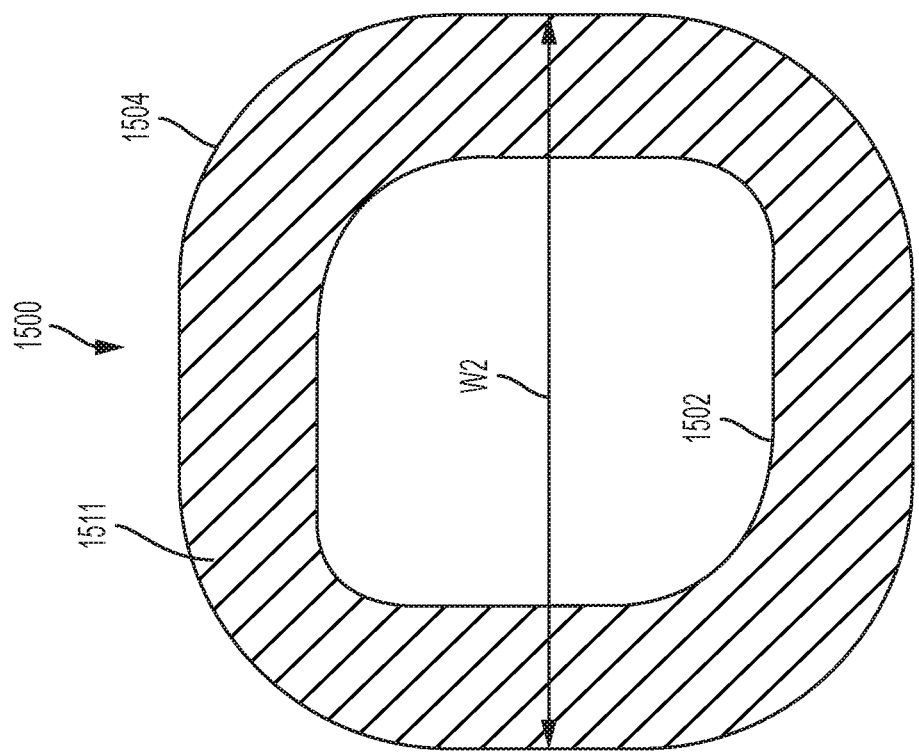
FIG. 60 is a perspective view of a square ring shaped barrier extender having a second width and having an oval opening according to an embodiment.
Figure 59:
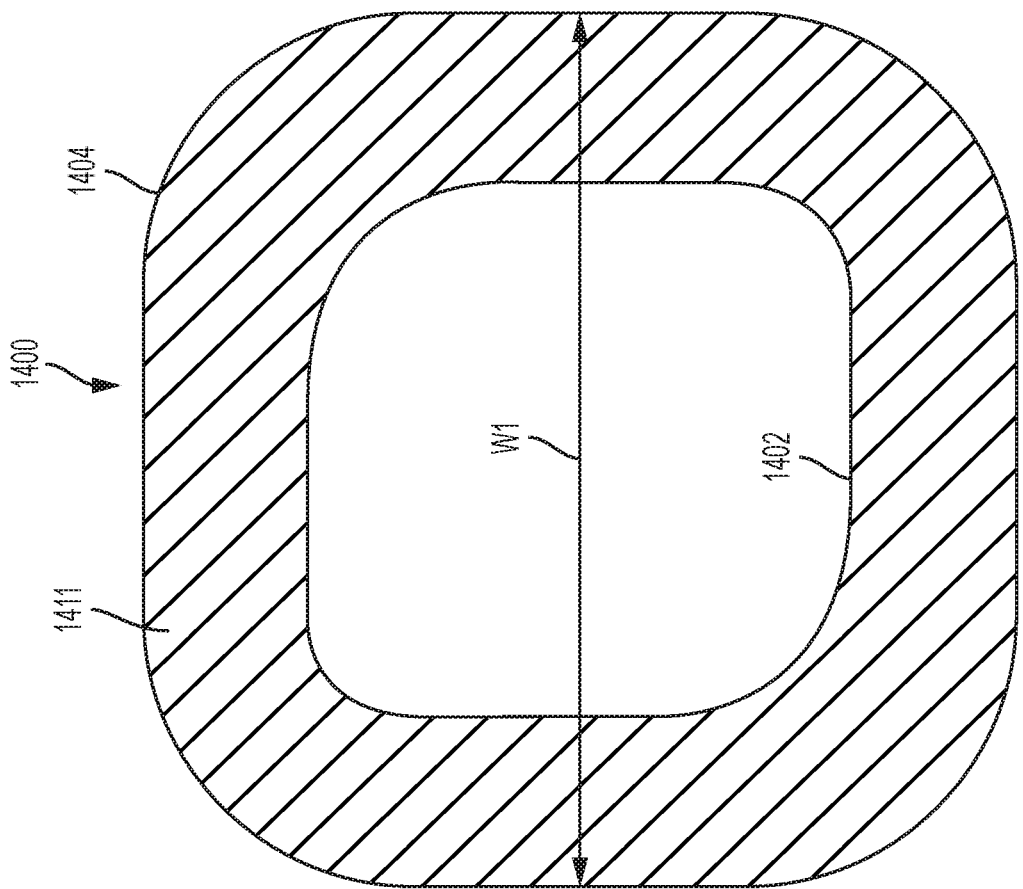
FIG. 59 is a perspective view of a square ring shaped barrier extender having a first width and having an oval opening according to an embodiment.

FIGS. 59 and 60 show differently sized barrier extenders 1400, 1500, according to an embodiment described herein. In the embodiments shown in FIGS. 59 and 60, the barrier extenders are shown as blanks, or non-perforated. Referring to FIG. 59, in one embodiment, the barrier extender 1400 has a generally oval inner periphery 1402, a generally square outer periphery 1404, and a ring shaped body 1411 defined therebetween. The barrier extender 1400 has a first width W1. In one embodiment, the first width W1 may be about 6.5 inches, but is not limited thereto.

Referring to FIG. 60, in one embodiment, the barrier extender 1500 has a generally oval inner periphery 1502, a generally square outer periphery 1504, and a ring shaped body 1511 defined therebetween. The barrier extender 1500 has a second width W2. In one embodiment, the second width W2 may be about 5.5 inches, but is not limited thereto. Thus, the barrier extenders 1400, 1500 shown in FIGS. 59 and 60 may be manufactured having different sizes. As such, in the embodiments described herein, the barrier extender may be manufactured in different sizes to overlay differently sized or shaped ostomy skin barriers.

FIGS. 61-64 show examples of different perforation lines that may be formed in the ostomy barrier extender 1400, 1500, according to embodiments described herein. For example, referring to FIG. 61, the ostomy barrier extender 1400, 1500 may include two perforated lines 1424, 1426. The perforated lines 1424, 1426 may be formed on opposite sides of the of the ostomy barrier extender 1400, 1500 and extend from the inner periphery 1402, 1502 to the outer periphery 1404, 1504. However, the present disclosure is not limited to such a configuration. For example, the perforated lines 1424, 1426 may be formed on adjacent sides, opposite or adjacent corners, or combinations of a side and a corner.

In other embodiments, for example as shown in FIGS. 62 and 63, the ostomy barrier extender 1400, 1500 may include four perforated lines 1424, 1426, 1428, 1430. The perforated lines 1424, 1426, 1428, 1430 may extend from the inner periphery 1402, 1502 to the outer periphery 1404, 1504. Referring to FIG. 62, in one embodiment, the perforated lines 1424, 1426, 1428, 1430 may be formed on respective sides 1432, 1434, 1436, 1438 of the ostomy barrier extender 1400, 1500. In another embodiment, as shown in FIG. 63, the perforated lines 1424, 1426, 1428, 1430 may be formed on respective corners 1440, 1442, 1444, 1446. In other embodiments, the perforated lines may be formed at various combinations of the sides and corners.

Referring to FIG. 64, in one embodiment, the ostomy barrier extender 1400, 1500 includes a perforated line 1424 and a split 1448 defined by a gap extending between the inner periphery 1402 and the outer periphery 1404. In one embodiment, the split 1448 and the perforated line 1424 may be positioned approximately 180 degrees from one another, but the present disclosure is not limited such relative positioning. Further, in one embodiment, the split 1448 and the perforated line 1424 may be formed on opposite sides of the ostomy barrier extender 1400, 1500. However, it is understood that the split 1448 and the perforated line 1424 may be formed on the same side, adjacent sides, opposing corners, adjacent corners or on combinations of the sides and corners.

Figure 65:
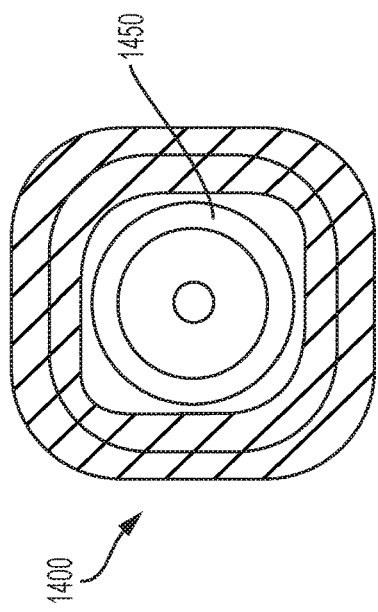
FIG. 65 is a schematic illustration of the square ring shaped ostomy barrier extender having an oval opening of FIG. 59 used to overlay a square shaped ostomy skin barrier having a first width according to an embodiment.
Figure 69:
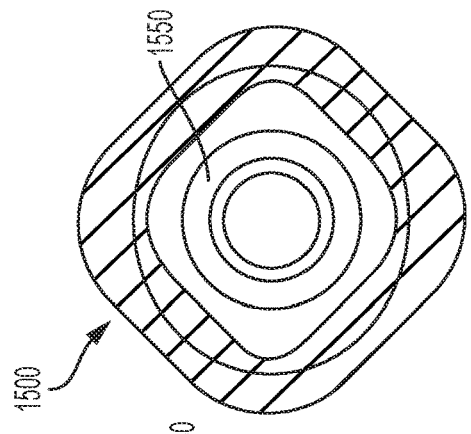
FIG. 69 is a schematic illustration of the square ring shaped ostomy barrier extender having an oval opening of FIG. 60 used to overlay another oval shaped ostomy skin barrier according to an embodiment.
Figure 68:
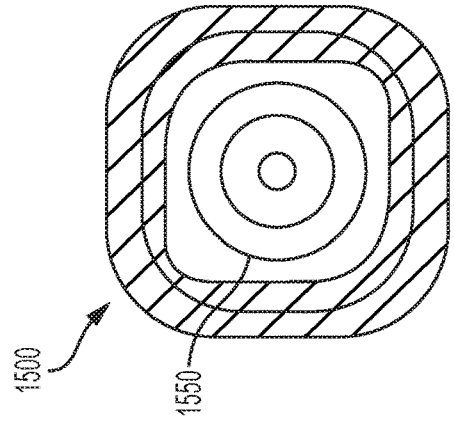
FIG. 68 is a schematic illustration of the square ring shaped ostomy barrier extender having an oval opening of FIG. 60 used to overlay an oval shaped ostomy skin barrier according to an embodiment.
Figure 67:
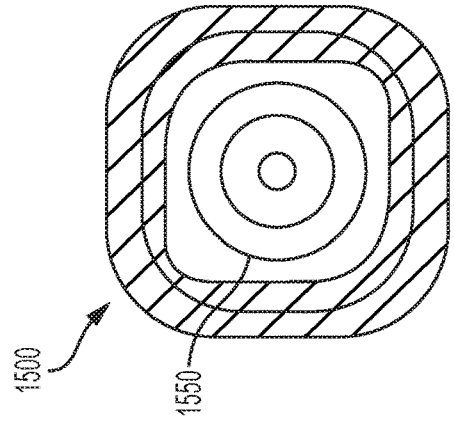
FIG. 67 is a schematic illustration of the square ring shaped ostomy barrier extender having an oval opening of FIG. 60 used to overlay another square shaped ostomy skin barrier having a second width according to an embodiment.
Figure 66:
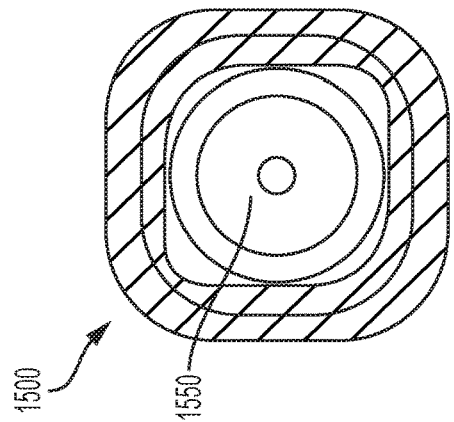
FIG. 66 is a schematic illustration of the square ring shaped ostomy barrier extender having an oval opening of FIG. 60 used to overlay a square shaped ostomy skin barrier having a second width according to an embodiment.

FIG. 65 is a schematic illustration of the ring shaped ostomy barrier extender 1400 having an oval inner periphery of FIG. 59 overlaying a square shaped ostomy skin barrier 1450 having a first size according to an embodiment. FIG. 66 is a schematic illustration of the ring shaped ostomy barrier extender 1500 having an oval inner periphery of FIG. 60 overlaying a square shaped ostomy skin barrier 1550 having a second size, less than the first size, according to an embodiment. FIG. 67 is a schematic illustration of the ring shaped ostomy barrier extender 1500 having an oval inner periphery of FIG. 60 overlaying another square shaped ostomy skin barrier 1550 according to an embodiment. In FIG. 68, the barrier extender 1500 is applied at a rotationally offset angle relative to an oval skin barrier 1550, and when compared to the position of the ostomy barrier extender 1500 shown in FIGS. 66 and 67. For example, in one embodiment, the barrier extender 1500 is rotated approximately 45 degrees relative to the oval skin barrier 1550. FIG. 69 shows the barrier extender applied at the rotationally offset angle described with respect to FIG. 68, on another oval skin barrier 1550, according to an embodiment described herein.

In the embodiments above, differently shaped ostomy barrier extenders, i.e., ostomy barrier extenders having differently shaped inner peripheries and/or outer peripheries may be used to provide different areas of coverage with different ostomy skin barriers.

It is understood that various features from any of the above embodiments may be implemented into, used together with, or replace features in any of the other embodiments above, and that such combinations or modifications are within the scope of the disclosure.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. An ostomy barrier extender comprising:
a skin friendly adhesive layer;
a backing layer laminated on a surface of the skin friendly adhesive layer;
a release liner laminated on an opposite surface of the skin friendly adhesive layer;
at least one perforated feature;
an outer periphery;
an inner periphery; and
a ring shaped body defined between the outer periphery and the inner periphery,
wherein the at least one perforated feature comprises a generally straight perforated line that extends between the inner periphery and the outer periphery and curved perforated lines that extend from the outer periphery proximate the generally straight perforated line to another edge of the outer periphery such that the curved perforated lines form a circular outline together, wherein the ostomy barrier extender is configured to separate along the at least one perforated feature, wherein the ostomy barrier extender is configured as a single-piece extender for overlaying and circumscribing around a periphery of an ostomy skin barrier which can be divided into at least two separate extender pieces by separating the ostomy barrier extender along the at least one perforated feature, wherein each extender piece is configured to overlay a portion of the periphery of the ostomy skin barrier, and
wherein when separated at the at least one perforated feature, the ostomy barrier extender less than fully circumscribes the periphery of the ostomy skin barrier.

2. The ostomy barrier extender of claim 1, wherein the perforated feature is at least one perforated line, and wherein the ostomy barrier extender further comprises a split defined by a gap between two ends of the ring shaped body.

3. The ostomy barrier extender of claim 2, wherein the perforated line and the split extend on the ring shaped body at about 180 degrees from one another.

4. The ostomy barrier extender of claim 1, wherein the at least one perforated feature is at least two perforated lines, each perforated line extending from the inner periphery to the outer periphery.

5. The ostomy barrier extender of claim 4, wherein two perforated lines extend on the ring shaped body at about 180 degrees from one another.

6. The ostomy barrier extender of claim 1, wherein the at least one perforated feature is at least four perforated lines, each perforated line extending from the inner periphery to the outer periphery.

7. The ostomy barrier extender of claim 6, wherein four perforated lines extend on the ring shaped body at about 90 degrees from one another.

8. The ostomy barrier extender of claim 1, wherein the outer periphery is square and the inner periphery is square, and the outer and inner periphery squares have rounded corners.

9. The ostomy barrier extender of claim 1, wherein outer periphery is square and the inner periphery is circular, and the square has rounded corners.

10. The ostomy barrier extender of claim 1, wherein the outer periphery is square and the inner periphery is oval, and the square has rounded corners.

11. The ostomy barrier extender of claim 1, wherein the skin friendly adhesive layer comprises hydrocolloid.

12. The ostomy barrier extender of claim 1, wherein the backing layer is formed from a thin urethane film.

13. The ostomy barrier extender of claim 1, wherein the at least one perforated feature extends through the backing layer and the skin friendly adhesive layer.

14. The ostomy barrier extender of claim 1, wherein the at least one perforated feature extends through the backing layer, skin friendly adhesive layer, and the release liner.

* * * * *